(12) United States Patent
Henzl et al.

(10) Patent No.: US 12,151,247 B1
(45) Date of Patent: Nov. 26, 2024

(54) HIGH EFFICIENCY ENVIRONMENTAL SAMPLING WITH RAPIDLY CURED PEELABLE COATINGS

(71) Applicant: Triad National Security, LLC, Los Alamos, NM (US)

(72) Inventors: Vladimir Henzl, Los Alamos, NM (US); Rollin Lakis, Los Alamos, NM (US); Sylvia Ann Junghans, Los Alamos, NM (US)

(73) Assignee: TRIAD NATIONAL SECURITY, LLC, Los Alamos, NM (US)

( * ) Notice: Subject to any disclaimer, the term of this patent is extended or adjusted under 35 U.S.C. 154(b) by 96 days.

(21) Appl. No.: 17/141,107

(22) Filed: Jan. 4, 2021

Related U.S. Application Data

(63) Continuation of application No. 15/785,295, filed on Oct. 16, 2017, now Pat. No. 10,883,901.
(Continued)

(51) Int. Cl.
| | | |
|---|---|---|
| *G01N 1/02* | (2006.01) | |
| *B01L 7/00* | (2006.01) | |
| *C12Q 1/686* | (2018.01) | |

(52) U.S. Cl.
CPC ............... *B01L 7/52* (2013.01); *G01N 1/02* (2013.01); *B01L 2300/069* (2013.01);
(Continued)

(58) Field of Classification Search
CPC ...... G01N 1/02; G01N 2001/028; C08F 2/48; B01J 20/291; B01J 20/286; B01J 20/3208;
(Continued)

(56) References Cited

U.S. PATENT DOCUMENTS 3,023,122 A 2/1962 De Pataky
6,664,357 B1 * 12/2003 Edelman ............. C08F 290/067
526/321
(Continued)

OTHER PUBLICATIONS

Hu, Fei, et al., "Smart Liquid SERS Substrates based on Fe3O4/Au Nanoparticles with Reversibly Tunable Enhancement Factor for Practical Quantitative Detection", Scientific Reports (2014), 4:7204, DOI:10.1038, pp. 1-10.
(Continued)

*Primary Examiner* — Maureen Wallenhorst
(74) *Attorney, Agent, or Firm* — Lewis Roca Rothgerber Christie LLP

(57) ABSTRACT

A rapidly curable liquid gel for collecting an analyte from a sampling surface includes a polymer precursor mixture including a monomer and/or an oligomer; and an additive to enhance extraction of the analyte from the sampling surface. A kit for collecting an analyte from a sampling surface may include the rapidly curable liquid gel and a portable device for rapidly curing the gel. The rapidly curable liquid gel is cured to thereby form a peelable sampling film, and the sampling film is removed from the sampling surface, thereby collecting the analyte. In one embodiment, the rapidly curable liquid gel is UV-curable, the polymer precursor mixture further includes a photoinitiator compound, and the portable device includes a UV light source configured to emit UV light of a wavelength range absorbed by the photoinitiator compound.

19 Claims, 11 Drawing Sheets

Related U.S. Application Data

(60) Provisional application No. 62/408,589, filed on Oct. 14, 2016.

(52) U.S. Cl.
CPC ............... *B01L 2300/0825* (2013.01); *B01L 2300/1861* (2013.01); *C12Q 1/686* (2013.01); *G01N 2001/028* (2013.01)

(58) Field of Classification Search
CPC ...... C08L 33/08; B01L 7/52; B01L 2300/069; B01L 2300/0825; B01L 2300/1861; C12Q 1/686; C09D 4/00
USPC .................... 435/6.1, 6.12; 436/164, 174
See application file for complete search history.

(56) References Cited

U.S. PATENT DOCUMENTS

| | | | |
|---|---|---|---|
| 8,658,580 | B2 | 2/2014 | Kaminski et al. |
| 10,883,901 | B1* | 1/2021 | Henzl ............... B01J 20/286 |
| 2005/0230267 | A1 | 10/2005 | Veatch et al. |
| 2011/0250442 | A1* | 10/2011 | Castro ............... C08J 7/0427 977/773 |
| 2014/0274660 | A1 | 9/2014 | Kabir et al. |
| 2015/0240115 | A1 | 8/2015 | Larsen et al. |
| 2016/0202149 | A1 | 7/2016 | Thomson et al. |
| 2016/0288940 | A1* | 10/2016 | Belt ............... A61L 31/14 |

OTHER PUBLICATIONS

Jimenez-Sandoval, S., "Micro-Raman spectroscopy: a powerful technique for materials research", Microelectronics Journal (2000) 3:419-427.

Lee, Sangmin, et al., "Light Output of Plastic Scintillators Fabricated by UV Curling", Transactions of the Korean Nuclear Society Spring Meeting, Jeju, Korea, May 18-19, 2017, 3 pps.

Zhu, Jun, et al., "Preparation and characterization of a novel UV-curable plastic scintillator", Nuclear Instruments and Methods in Physics Research A (2016) 828:30-34.

* cited by examiner

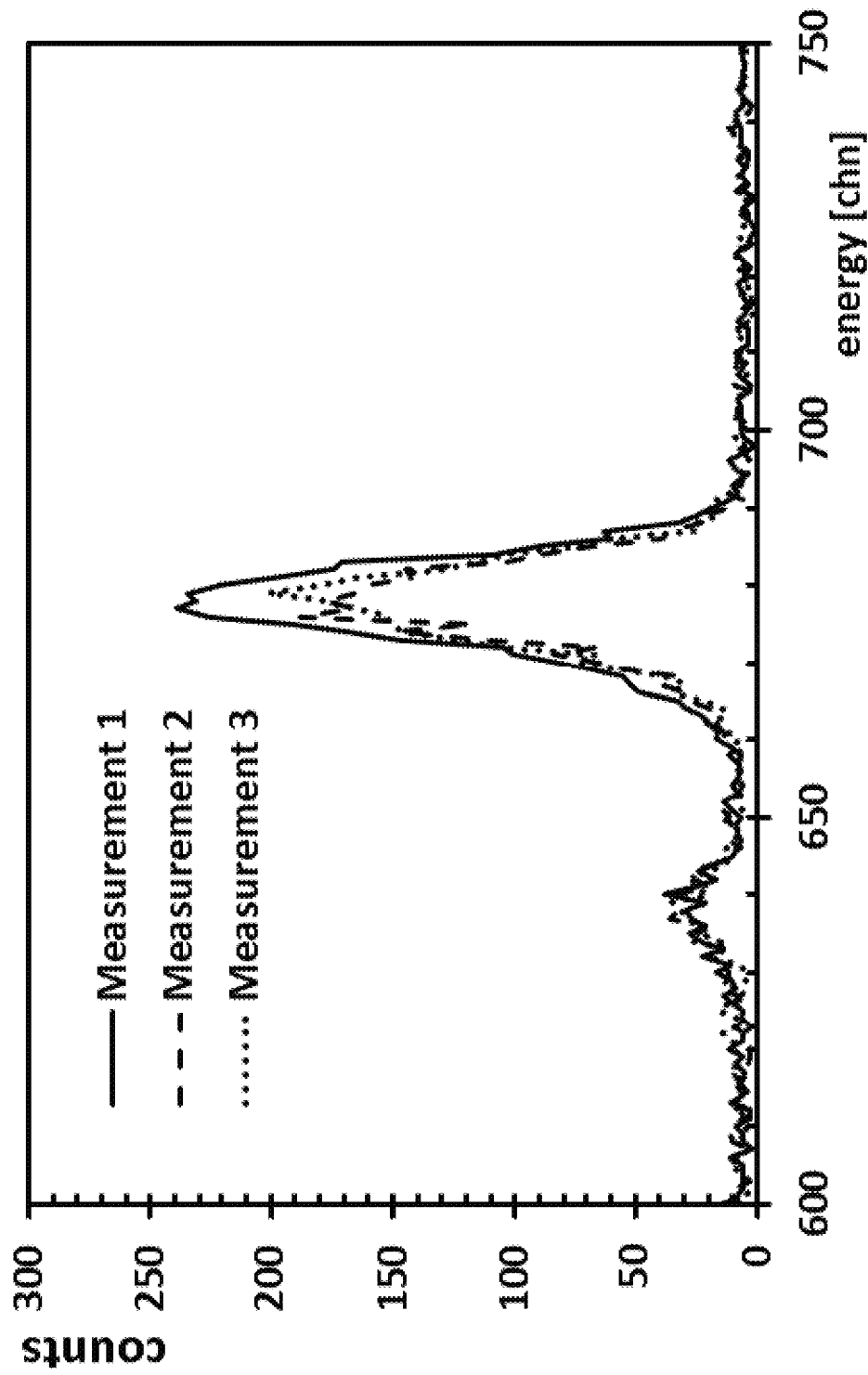

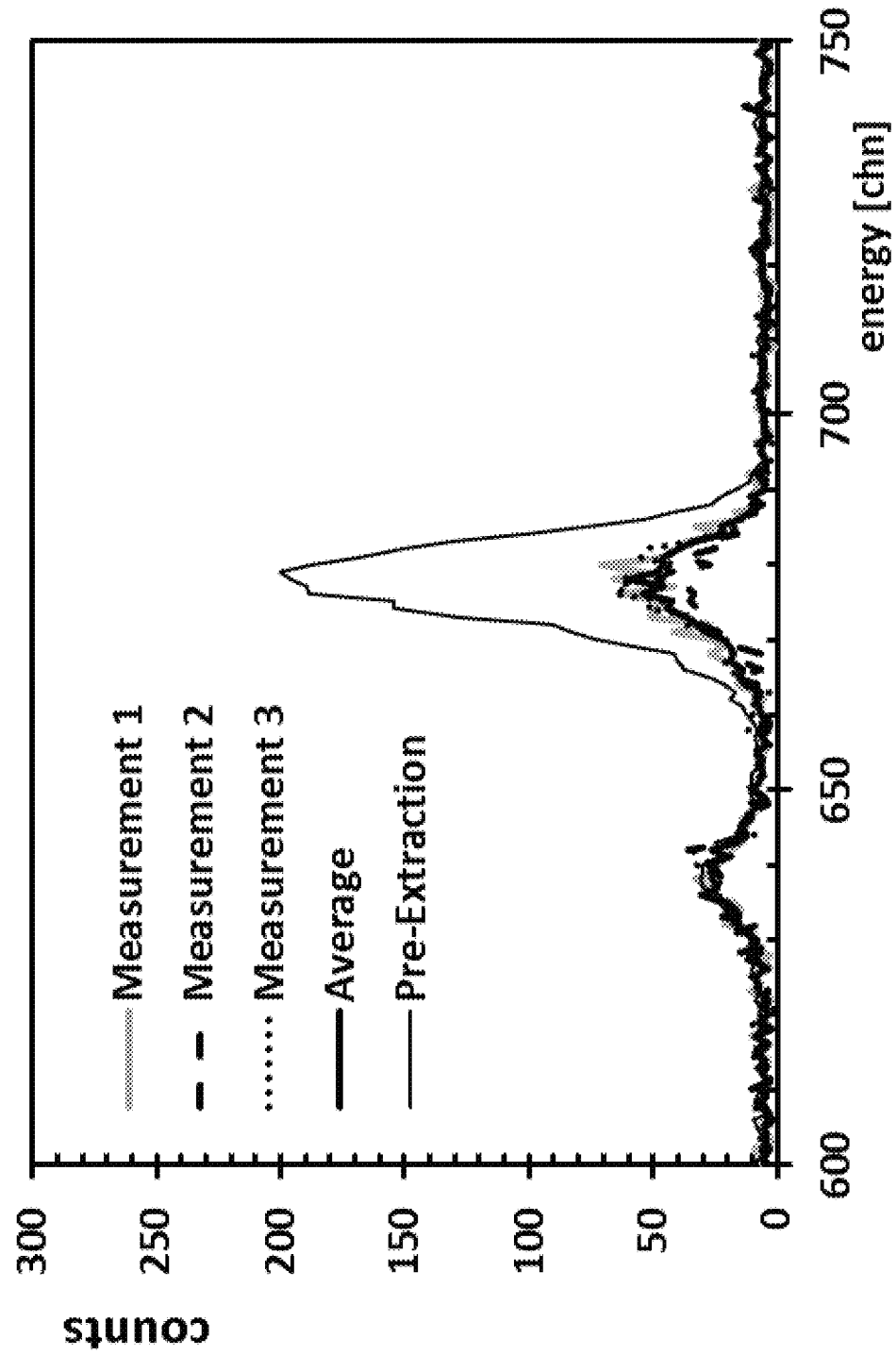

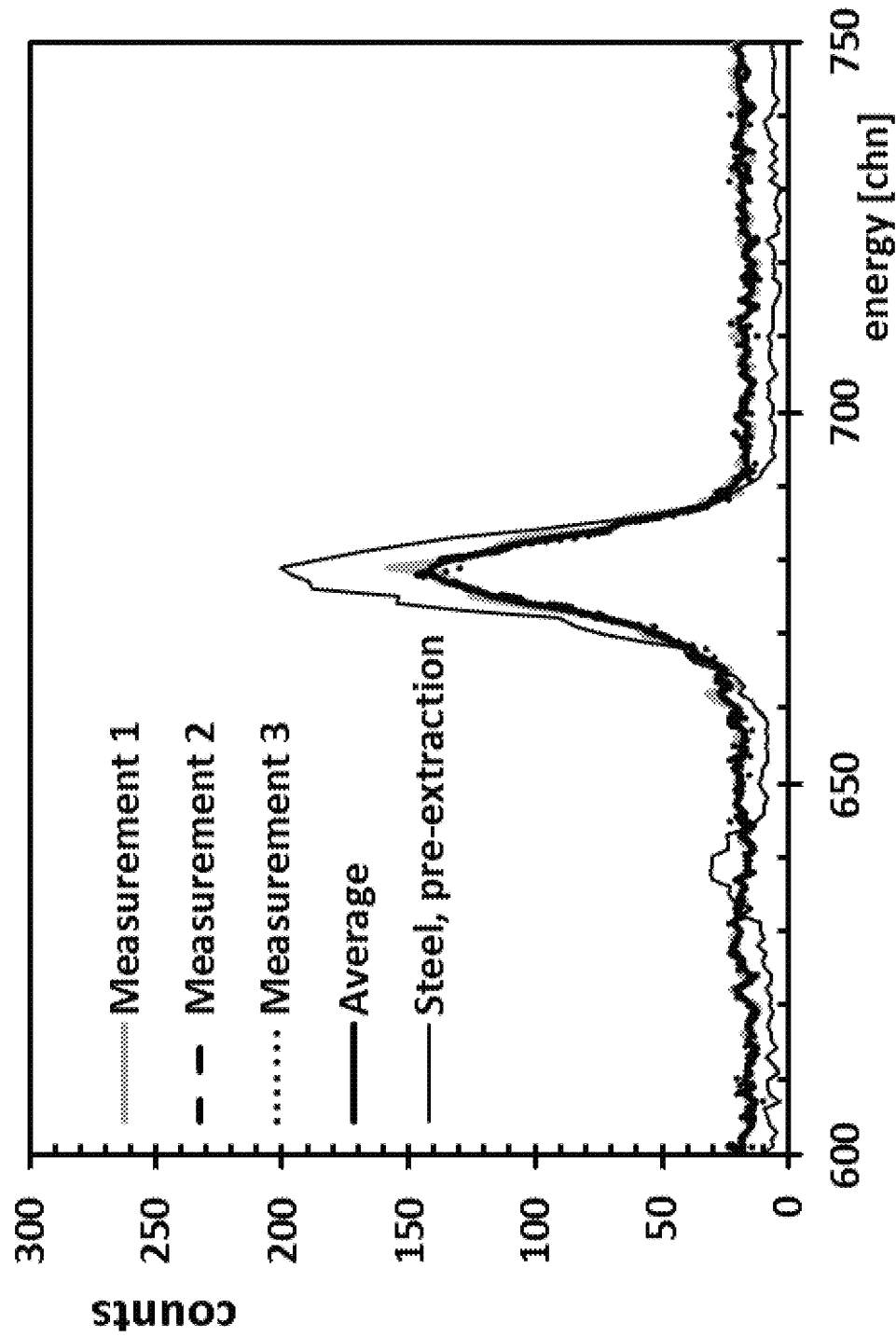

HIGH EFFICIENCY ENVIRONMENTAL SAMPLING WITH RAPIDLY CURED PEELABLE COATINGS

CROSS-REFERENCE TO RELATED APPLICATION

This application is a continuation of and claims priority to and the benefit of U.S. patent application Ser. No. 15/785,295 filed Oct. 16, 2017, now U.S. Pat. No. 10,883,901, which claims priority to and the benefit of U.S. Provisional Application No. 62/408,589, filed Oct. 14, 2016 and titled "HIGH EFFICIENCY ENVIRONMENTAL SAMPLING WITH RAPIDLY CURED PEELABLE COATINGS," the entire contents of all which are incorporated herein by reference.

STATEMENT REGARDING FEDERALLY SPONSORED RESEARCH OR DEVELOPMENT

The United States government has certain rights in this invention pursuant to Contract No. DE-AC52-06NA25396 between the United States Department of Energy and Los Alamos National Security, LLC for the operation of Los Alamos National Laboratory.

BACKGROUND

Environmental sampling and forensic evidence collection is often performed by swiping a surface suspected to contain an analyte of interest with cotton swipes or swabs. The collection efficiency of such swipes or swabs is typically low (about 10% to less than 1% of the total environmental presence of the analyte), and strongly depends on the chemical and physical properties of the analyte as well as the type of surface from which the sample is collected. For example, the collection efficiency by cotton swipes of analytes embedded in surfaces of porous materials such as wood, concrete, or fabric is substantially or practically zero. Furthermore, the analyte collected by dry cotton swipe or swab is susceptible to being literally shaken off the loose cotton matrix during transport, resulting in further loss (typically about 10 percent or more of the total collected amount) of the analyte during transport or storage. Additionally, environmental and operator variations in swiping technique result in data that may be difficult to quantitatively interpret and reproduce.

Therefore, existing cotton swipe and swab based sample collection techniques and materials are often unsatisfactory for the accurate and sensitive detection of trace amounts of chemical, biological, radiological, nuclear, or explosive (CBRNE) material and are generally not suitable as means of preserving the collected sample as forensic evidence.

SUMMARY

According to embodiments of the present disclosure, a kit for collecting an analyte from a sampling surface includes a rapidly curable liquid gel and a portable device to enable rapid curing. The rapidly curable liquid gel may include a polymer precursor mixture including a monomer and/or an oligomer; and an additive selected to enhance extraction of the analyte from the sampling surface. In some embodiments, the kit may further include a stencil including openings through which a portion of the rapidly curable liquid gel can pass to directly contact the sampling surface.

In some embodiments, the rapidly curable liquid gel may further include a cure activator component including a hardener or catalyst configured to be mixed with the rapidly curable liquid gel prior to application of the rapidly curable liquid gel to the sampling surface.

In some embodiments, the polymer precursor mixture may include an acrylic resin that is polymerized on exposure to water vapor.

In some embodiments, the rapidly curable liquid gel may include a photoinitiator compound. In some embodiments, the photoinitiator compound may absorb UV light around 365 nm and/or 395 nm.

In some embodiments, the monomer may include a styrene derivative, an N-vinylpyrrolidone derivative, a polyol derivative, a vinyl derivative, an acrylate derivative, or a combination thereof. In some embodiments, the monomer may be selected from N-vinylpyrrolidone, 1,4-butanediol, 1,5-pentanediol, tri(ethylene glycol)divinyl ether, isobornyl acrylate, di(ethylene glycol)ethyl ether acrylate, tetrahydrofurfuryl acrylate, trimethylolpropane triacrylate, 2-[[(butylamino)carbonyl]oxy]ethyl acrylate, 2-hydroxy-3-phenoxypropyl acrylate, di(ethylene glycol) 2-ethylhexyl ether acrylate, poly(propylene glycol) acrylate, soybean oil epoxidized acrylate, dipentaerythritol penta-/hexa-acrylate, butyl acrylate, tri(propylene glycol) diacrylate, and combinations thereof.

In some embodiments, the oligomer may be selected from an acrylated epoxy derivative, a urethane derivative, a polyether derivative, a polyester derivative, or a combination thereof.

In some embodiments, the additive may be selected from a solvent, a ligand, a non-ionic detergent, or a combination thereof. In some embodiments, the solvent may be ethanol. In some embodiments, the ligand may be EDTA.

In some embodiments, the kit may further include an additional additive in the rapidly curable liquid gel to modulate its viscosity.

In some embodiments, the kit may further include a SERS-enabling nanoconfined structure in the rapidly curable liquid gel.

In some embodiments, the kit may further include a ligand in the rapidly curable liquid gel capable of forming a luminescent complex with the analyte.

In some embodiments, the kit may further include an additional additive in the rapidly curable liquid gel capable of emitting light in response to ionizing radiation produced by the analyte.

In some embodiments, the portable device to enable rapid curing may include a portable UV light source configured to emit UV light of a wavelength range absorbed by the photoinitiator compound.

According to embodiments of the present disclosure, a method of using the kit for collecting an analyte from a sampling surface includes applying the rapidly curable liquid gel to the sampling surface; curing the rapidly curable liquid gel using the portable device to enable rapid curing to yield a sampling film including the analyte; and removing the sampling film including the analyte from the sampling surface.

In some embodiments, the method further includes storing the sampling film including the analyte in a container.

According to embodiments of the present disclosure, a composition for a rapidly curable liquid gel, the composition being configured to collect an analyte from a sampling surface, includes: a polymer precursor mixture comprising a monomer and/or an oligomer; and an additive selected to enhance extraction of the analyte from the sampling surface. In some embodiments, the composition may further include a photoinitiator compound.

BRIEF DESCRIPTION OF THE DRAWINGS

These and other features and advantages of embodiments of the present invention will be better understood by reference to the following detailed description when considered in conjunction with the accompanying drawings.

FIGS. 4A to 4C are graphs showing representative XRF spectra used to determine the sampling efficiencies of an example rapidly cured liquid gel composition on a steel surface, according to embodiments of the present disclosure. FIG. 4A is a graph of XRF spectra taken of a steel sampling surface prior to sampling. FIG. 4B is a graph of XRF spectra taken of the same steel sampling surface as in FIG. 4A after sampling with the rapidly cured liquid gel composition according to Example 3-6. FIG. 4C is a graph of XRF spectra taken of the cured sampling film produced from the rapidly cured liquid gel composition according to Example 3-6, according to embodiments of the present disclosure.

DETAILED DESCRIPTION

Figure 1A:
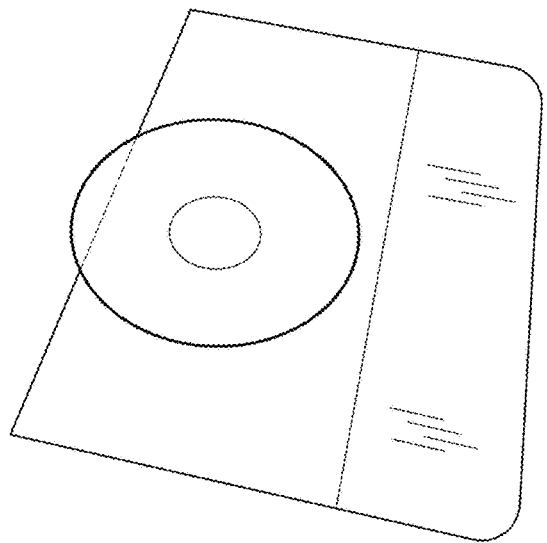
FIGS. 1A to 1D are photographic images depicting various steps in an example step-by-step process for collecting an environmental sample, according to embodiments of the present disclosure.

Aspects of example embodiments of the present disclosure are directed toward one or more rapidly curable liquid gel compositions used to efficiently and reproducibly collect trace amounts (e.g., microgram or smaller amount) of substances or analytes from various sampling surfaces and operational environments. While the rapidly curable liquid gel compositions are particularly useful for collecting trace amounts of substances and analytes, it is understood that the compositions are also suitable for the collection of larger amounts (i.e. milligram to gram amounts) of substances and analytes. The compositions according to embodiments of the invention may be used to collect any suitable amount of a substance or analyte.

The substances or analytes for collection (referred to herein interchangeably as "analytes", "samples", and the like) may be any substance capable of being trapped, embedded, or otherwise captured in a sampling film resulting from rapid curing of the liquid gel composition. For example, in some embodiments, the analyte may be a chemical, biological, radiological, nuclear, or explosive (CBRNE) sample; however, the analyte is not limited to these categories. In some embodiments, the analyte may be considered a contaminant (e.g., an unwanted material or impurity).

As used herein, the term "chemical sample(s)" and like terms may refer to any material that is to be quantified or identified based on its elemental composition, molecular structure, chemical properties, chemical reactivity, or reaction to electromagnetic energy stimuli or input (e.g., chemical spectra). Non-limiting examples of chemical samples may include organic or inorganic substances, for example, gun powder and gunshot resides, physiologically active and psychoactive substances (e.g., drugs, poisons, and pharmaceuticals), chemical warfare agents, hydrocarbons and fire accelerants, paint, polymer, and plastic particles, fibers, dirt, adhesives, heavy metals, etc.

As used herein, the term "biological sample(s)" and like terms may refer to any material of biological origin or material that is produced within a biological system, such as a plant, animal, microorganism, or cell. Non-limiting examples of biological samples may include fingerprints, tissues (such as skin and hair), residue from fluids (such as saliva, blood, and semen), nucleic acid polymers (such as DNA and/or RNA), proteins, lipids, microorganisms and microflora (such as bacteria, viruses, and fungi), and cells (e.g., mammalian cells).

As used herein, the terms "radiological sample(s)," "nuclear sample(s)", "nuclear contaminants", and like terms may refer to any material that emits ionizing radiation, includes atoms or nuclear isotopes exhibiting radioactivity, or otherwise spontaneously undergoing nuclear decay. Non-limiting examples of such atoms may include isotopes of uranium (U), plutonium (Pu), thorium (Th), and the like. The term "special nuclear material" (SNM) is used herein in its art-recognized sense to refer to particular isotopes of U and Pu, e.g., plutonium-239, uranium-233, uranium enriched in the isotopes uranium-233 or uranium-235, etc. The sizes and shapes of nuclear contaminants are not particularly limited, and may include particles having millimeter scale or micron scale diameters. The type of radiation emitted by the nuclear contaminants may include alpha-, beta-, gamma, and neutron-radiation.

As used herein, the term "explosive samples" and like terms may refer to any material storing a large amount of potential energy that, upon a stimulus (such as heat, spark, friction, and/or impact) suddenly releases the energy in the form of light, heat, sound, and/or pressure. Non-limiting examples of explosive samples may include nitro-group containing organic compounds (such as nitroglycerin, TNT, nitrourea, octogen, picric acid, nitrocellulose, etc.), azide-containing compounds (such as sodium azide, lead azide, barium azide, 2-dimethylaminoethylazide, etc.), nitrate-containing compounds (such as sodium nitrate, calcium nitrate, ammonium nitrate, etc.), peroxides, perchlorates, and mixtures such as blasting powder, etc.

As used herein, the term "substantially" is used as a term of approximation and not as a term of degree, and is intended to account for the inherent inaccuracies in measured, observed, or calculated values or qualities. For example, the term "substantially zero" as used herein to refer to the sampling efficiency of a cotton swipe on a porous material means that the sampling efficiency is so low that the detectable amount of analyte is effectively indistinguishable from a negative control.

According to one or more embodiments of the present invention, a rapidly curable liquid gel may be used to collect an analyte from a sampling surface. As used herein, the term "rapidly curable", as used to describe a liquid gel or liquid gel composition, refers to a material or composition that can be converted from a liquid material or mixture to a solid material within an amount of time suitable for efficient and effective sample collection (e.g., a timescale of a few seconds to a few minutes). In some embodiments, the rapidly curable liquid gel is poured onto (or otherwise applied to) a surface including an analyte or sample intended for collection, and then rapidly cured to form a peelable sampling film (e.g., peelable coating). As used herein, the term "peelable" refers to a characteristic of being easily removed or detached from a surface as a single piece, for example, as a continuous thin layer. The peelable sampling film may absorb, enclose, be impregnated with, or otherwise be capable of retaining the analyte with low or reduced rates of analyte loss during storage and transport.

The rapidly curable liquid gel composition may be cured (e.g., physically transformed into a solid material) via any suitable reaction mechanism. In some embodiments, for example, the rapidly curable liquid gel composition (or liquid gel) includes a rapidly curable polymer precursor mixture that is stable under storage conditions, and can be induced to undergo polymerization under specific conditions (e.g., a trigger) applied by the user. For example, the polymer precursor mixture in the rapidly curable liquid gel may be designed or selected to be polymerized upon removal of a component, addition of a chemical input or catalyst, exposure to a specific energy input, or a combination of the above.

In some embodiments, for example, the polymer precursor mixture in the rapidly curable liquid gel may undergo polymerization upon evaporation of a volatile inhibiting substance, or upon concentration of the mixture upon evaporation of a volatile solvent, for example, upon heating. In other embodiments, the polymer precursor mixture may undergo polymerization upon addition of one or more additional chemicals. In some embodiments, for example, the polymer precursor mixture may have a composition and/or polymerization mechanism similar to cyanoacrylate glue, in which polymerization of an acrylic resin is induced by exposure to hydroxide ions in ambient water vapor. In another example, the polymer precursor mixture may have a composition and/or polymerization mechanism similar to an epoxy resin, in which a cure activator component including a hardener or catalyst is mixed with the polymer precursor mixture to thereby induce polymerization.

In some embodiments, the polymerization of the polymer precursor mixture may be triggered (e.g., induced) by addition of energy, for example, light energy or heat energy. In some embodiments, when polymerization is triggered by ultraviolet (UV) light energy, the rapidly curable liquid gel may be referred to as a UV-curable liquid gel including a UV-curable polymer precursor mixture. The term "UV-curable", as used herein to describe a liquid gel, polymer precursor mixture, or coating composition, refers to a material, mixture, or composition that undergoes polymerization of its components upon exposure to ultraviolet (UV) light energy (e.g., light energy having a wavelength between about 10 nm to about 400 nm). It will be understood that although embodiments of the present disclosure in which the rapidly curable liquid gel is a UV-curable liquid gel are described in more detail below, the scope of the present disclosure is not limited thereto, and that a skilled artisan is capable of selecting other rapidly curable liquid gels according to the principles described herein.

In some embodiments, when the rapidly curable liquid gel is a UV-curable liquid gel including a UV-curable polymer precursor mixture, the UV-curable polymer precursor mixture may include a photoinitiator compound and one or more monomers or oligomers. Upon exposure to UV light, the compounds included in the UV-curable polymer precursor mixture may undergo one or more photoinitiated polymerization (photopolymerization) reactions to form a solid material including a polymer network. The photoinitiator compound mediates initial activation of the photopolymerization reactions, and may be any compound capable of absorbing UV light energy and transferring that energy to a monomer or oligomer, thereby converting the monomer or oligomer into a reactive species that can then participate in chemically spontaneous photopolymerization reactions.

The photopolymerization reactions for forming a solid polymer network are not limited or bound to any particular reaction or mechanism, and may include cationic polymerization, free radical polymerization, and free radical promoted cationic polymerization. In some embodiments, the photopolymerization reactions may proceed via free radical polymerization. Accordingly, the photoinitiator may be any compound that is converted to a free radical species and/or converts a monomer or oligomer into a free radical species upon irradiation with UV light.

Because photoinitiators typically absorb only certain wavelength ranges of UV light energy, and UV light sources generally emit only certain wavelength ranges of UV light energy, the photoinitiator (photoinitiator compound) and light source should be selected so that they absorb energy and emit energy, respectively, within similar or overlapping wavelength ranges. For example, in some embodiments, the photoinitiator may absorb UV light between 200 nm to 400 nm, for example, between 315 nm to 400 nm. In some embodiments, the photoinitiator may absorb UV light around 365 nm and/or 395 nm. The UV light source may emit UV light within the above described ranges or at about the above described wavelengths.

The photoinitiator may be any suitable photoinitiator. In some embodiments, the photoinitiator may be a diarylketone compound. Non-limiting examples of the photoinitiator may include 4,4'-bis(diethylamino)benzophenone, Michler's ketone, 4-(dimethylamino)benzophenone, phenylbis(2,4,6-trimethylbenzoyl)-phosphine oxide (BAPO) and thioxanthen-9-one.

The amount of photoinitiator with respect to the total volume of monomer and/or oligomer in the UV polymer precursor mixture may be about 0.001 g/mL to about 0.03 g/mL, for example, about 0.015 g/mL to about 0.025 g/mL. However, embodiments of the present disclosure are not limited thereto, and the amount of photoinitiator may be suitably selected based on the specific combination of photoinitiator(s), monomer(s), and other components.

The monomer(s) in the UV-curable polymer precursor mixture may each be selected based on their compatibility with the photoinitiator, e.g., their ability to react with (e.g., receive energy from) the photoinitiator after activation. In some embodiments, this reactivity may be at least partially determined by the co-solubility (miscibility) of the monomers with the photoinitiator in the polymer precursor mixture. For example, the effective concentrations of the monomer and photoinitiator should increase with increased co-solubility, leading to a faster reaction according to Le Chatelier's principle. Accordingly, in some embodiments, the monomer may be selected according to its co-solubility or miscibility with the photoinitiator. In addition, the monomer(s) may include one or more functional groups that enable them to intermolecularly react with each other during propagation of the photopolymerization reactions. Non-limiting examples of such functional groups may include a vinyl group, an alcohol group, an ether group, a urethane group, an epoxy group, and an acryloyl group.

The monomer may be any suitable monomer for yielding a UV-curable composition. Non-limiting examples of suitable monomers include styrene derivatives, N-vinylpyrrolidone derivatives, polyol derivatives, vinyl derivatives, acrylate derivatives, and combinations thereof. In some embodiments, for example, the monomer may include, without limitation, N-vinylpyrrolidone, 1,4-butanediol, 1,5-pentanediol, tri(ethylene glycol)divinyl ether, isobornyl acrylate, di(ethylene glycol)ethyl ether acrylate, tetrahydrofurfuryl acrylate, trimethylolpropane triacrylate, 2-[[(butylamino)carbonyl]oxy]ethyl acrylate, 2-hydroxy-3-phenoxypropyl acrylate, di(ethylene glycol) 2-ethylhexyl ether acrylate, poly(propylene glycol) acrylate, soybean oil epoxidized acrylate, dipentaerythritol penta-/hexa-acrylate, butyl acrylate, tri(propylene glycol) diacrylate, and combinations thereof.

In some embodiments, the UV-curable composition may include one or more oligomers in addition to, or in place of, the monomer. The oligomer may be selected according to the same considerations described above for the monomer, and may be any suitable oligomer for yielding a UV-curable composition. Non-limiting examples of the oligomer may include acrylated epoxy derivatives, urethane derivatives, polyether derivatives, polyester derivatives, and combinations thereof. For example, the oligomer may include 2-carboxyethyl acrylate oligomers, poly(tetrahydrofuran), poly(vinylpyrrolidone), or a combination thereof.

In some embodiments, the UV-curable polymer precursor mixture may include a commercially available UV-curable coating composition, or a combination of commercially available UV-curable coating compositions. Commercial UV-curable coating compositions are available for a number of applications, including, for example, surface protection, paint masking, electronic masking, chemical and mechanical finishing operations, etc. Any such suitable commercial coating mixture may be used as long as the composition is UV-curable. Non-limiting examples of suitable commercially available UV-curable coating mixtures may include UV733 (General Chemical Corp, Brighton, MI), Tangent 20109 (Tangent Industries, Inc., Torrington, CT), and combinations thereof. In some embodiments, as mentioned herein, the UV-curable polymer precursor mixture may include a mixture of commercially available products. For example, a 50:50 combination of UV733 and Tangent 20109 was experimentally observed to produce films having suitable peelability and thicknesses for sampling, and curing times of about 5-10 seconds using an appropriate UV-light source. However, it is understood that any suitable mixing ratio may be used. In some embodiments, a commercially available UV-curable coating composition may be mixed with additional monomers, oligomers, and/or photoinitiators as discussed above.

While the rapidly curable or UV-curable polymer precursor mixture may make a sampling film with suitable peelability and thickness for sample and analyte collection applications, the polymer precursor mixture by itself may not have suitable affinity for the type of sample or analyte intended to be collected. Accordingly, the rapidly curable liquid gel for making the peelable sampling film according to embodiments of the present invention may further include one or more additives for improving the collection efficiency of the resulting peelable sampling film. For example, the one or more additives may modulate the material and functional characteristics of the rapidly curable liquid gel and/or the resultant peelable sampling film. Material characteristics may include the viscosity of the gel and the flexibility, peelability, and resistance to tearing of the cured sampling film. Functional characteristics may include the ability to enhance extraction of an analyte embedded in pores and cracks within a surface from which the analyte is being collected, the ability to later release the analyte from the sampling film for testing and analysis, and the ability to serve as a suitable medium or substrate for in situ detection and analysis of the analyte.

The additive may be selected based on the intended application of the peelable sampling film. For example, in some embodiments, the peelable sampling film may be configured for general use, i.e., to collect a variety of analytes from a variety of sample collection surfaces. In such embodiments, the additive may be selected so that the peelable sampling film is configured to extract commonly encountered analytes or samples (such as, e.g., metal particles, gunpowder, and crystalline organic material). In some embodiments, however, the additive can be selected to tailor the peelable sampling film to collect a particular type or class of analyte (e.g., chemical samples, nuclear samples, biological samples, explosive samples, etc.), and/or to collect analytes or samples from a particular type or class of sample collection surface (e.g., porous surfaces, smooth surfaces, etc.).

The additive may be any suitable additive for accomplishing the intended goal, as discussed above. The number and type of additives are not particularly limited, and combinations of additives may be used. Each additive may be used to achieve different goals (e.g., may target different analytes), and/or several additives may be used to achieve the same effect (e.g., may target the same analyte). Furthermore, some additives may impart multiple functions or characteristics to the rapidly curable liquid gel and/or the cured peelable sampling film.

In some embodiments, for example, the additive may include a solvent. The solvent may be any suitable solvent capable of mediating physical contact between, and mixing of an analyte and the rapidly curable liquid gel so that a detectable concentration of analyte may be absorbed in, adsorbed on, or otherwise included in the peelable sampling film after curing. In some embodiments, the solvent may be fully or at least partially soluble in the rapidly curable liquid gel. In some embodiments, the solvent may form a suspension in the rapidly curable liquid gel. In some embodiments, the solvent may be capable of solvating the target analyte. In some embodiments, the solvent may not completely solvate the target analyte, but may aid in the dispersion and spread of the rapidly curable liquid gel across the sampling surface, and/or aid in release and diffusion of the target analyte from the surface.

The amount of solvent is not particularly limited as long as the solvent does not form a completely separate, unmixed phase from the rapidly curable liquid gel. In some embodiments, the solvent may interfere with (e.g., reduce) the rate of curing, and as such, the amount of solvent may be selected to maintain a particular average curing time while also maintaining a suitable viscosity for enabling sufficient (and e.g., efficient) flow or spread of the rapidly curable liquid gel. In some applications, seepage of the rapidly curable gel into the surface may be undesirable, as this seepage may interfere with curing and removal of a peelable film (e.g., due to absorbance of UV light by the sampling surface, resulting in incomplete curing, and/or because the rapidly curable liquid gel is segregated into pores and cracks, resulting in formation of discontinuous cured plugs that are difficult to remove from the sampling surface). In these applications, some embodiments of the rapidly curable liquid gel may include enough solvent to allow for sufficient (and e.g., efficient) flow over the surface where the target analyte is located, but not so much solvent that the rapidly curable liquid gel seeps into the surface. For instance, the amount of solvent may be selected in order to prevent (or at least reduce) any such seepage into the surface. However, in other applications, seepage of the rapidly curable liquid gel into the surface may be desirable in order to attract or "pick up" analytes that have absorbed into the surface or that themselves have seeped into the surface. In these applications, some embodiments of the rapidly curable liquid gel may include enough solvent to enable the rapidly curable liquid gel to seep into the surface to the desired degree or depth. For instance, the amount of solvent may be selected to allow, enable or increase the degree or depth of seepage of the rapidly curable liquid gel. In some embodiments, for example, the amount of solvent may be selected so that the average curing time of the rapidly curable liquid gel is about 2 minutes or less, about 1 minute or less, or about 30 seconds or less. In some embodiments, when the rapidly curable liquid gel includes ethanol, the ethanol may be included in an amount of about 1 wt % to about 50 wt % based on the total weight of the liquid gel, for example, about 10 wt % to about 40 wt %, about 20 wt % to about 30 wt %, or about 25 wt %. In some embodiments, the solvent may be included up to its solubility limit in the rapidly curable liquid gel. For example, when the rapidly curable liquid gel includes urethane acrylate monomers or oligomers and the solvent is ethanol, the ethanol may be included in an amount of up to about 30 wt % based on the total weight of the liquid gel, for example about 1 wt % to about 30 wt %, about 5 wt % to about 25 wt %, or about 10 wt % to about 20 wt %.

In some embodiments, the solvent may be an aqueous solvent (e.g., water), a non-aqueous (organic) solvent (such as an alcohol, a hydrocarbon, an ether, a ketone, etc.), or a combination or mixture thereof. Non-limiting examples of the solvent may include water, methanol, ethanol, propanol, acetone, and hexane. In some embodiments, when the analyte includes a salt such as uranyl nitrate and/or plutonium nitrate, the solvent may include an alcohol, one non-limiting example of which is ethanol.

In some embodiments, for example when the analyte is a metal ion, the additive may include a ligand capable of producing a metal-ligand complex by binding to the metal ion. In some embodiments, the metal-ligand complex may have different solubility properties from the free metal ion, and may thereby aid in transfer of the metal ion from the sampling surface to the rapidly curable liquid gel. The ligand may be any suitable inorganic or organic ligand capable of binding to the metal ion, and may be selected according to the desired solubility properties of the metal-ligand complex in the liquid gel.

In some embodiments, the ligand may be a chelant (e.g., chelating ligand or agent). The chelant may be any suitable chelant, for example, an organic ligand containing two or more functional groups capable of coordinating to a cation, such as ethylene diamine (en), ethylene diamine tetraacetic acid (edetic acid, EDTA), 4,5-dihydroxy-1,3-benzenedisulfonic acid (tiron), sodium citrate dehydrate, L-cysteine, diethylenetriamine pentaacetic acid (DTPA), acetoacetonate (acac), oxalate, and combinations thereof. A strong thermodynamic driving force for binding of the chelant to the metal ion (e.g., the "chelate effect") may encourage formation of a metal-ligand complex. In some embodiments, for example when the polymer precursor mixture forms a polymer including functional groups that may act as analyte binding sites, the polymer itself may act as a chelate.

In some embodiments, the ligand and/or chelant may have varying affinities for different elements, and may be accordingly selected to "tune" the sensitivity of the sampling process towards specific elements and/or oxidation states of some elements in an analyte or sample targeted for collection.

In some embodiments, the ligand or chelant may be used solely to solubilize the metal ion or metal, and is not substantially involved in and/or does not substantially affect analysis of the metal. As used herein, the term "substantially" is used as a term of approximation and not as a term of degree, such that "not substantially involved in and/or does not substantially affect analysis of the metal" means that any effect of the ligand on the analysis of the metal is negligible. For example, the metal may be separated from the metal-ligand complex prior to or during analysis, or may be targeted for detection using a method that is insensitive to the presence or identity of a ligand.

In some embodiments, the metal-ligand complex may remain intact, and may itself be targeted as an analyte. Furthermore, in some embodiments, the metal-ligand complex may enable and/or enhance detection, for example, by improving the ability of an analysis technique to detect and/or distinguish between analytes or variants thereof (e.g., different elements, isotopes, oxidation states, etc.).

In some embodiments, when the additive is a chelant (such as EDTA), the chelant may be included at an amount of about 0.1 g to about 2 g per 10 mL of the rapidly curable liquid gel, for example, about 0.5 g to about 1 g per 10 mL of the UV-curable liquid gel.

In some embodiments, the additive may include or act as a sensitizer. As would be understood by those of ordinary skill in the art, the term "sensitizer" refers to a material that increases the ability of the analyte to be detected, for example, by decreasing the minimum concentration level required for positive detection, or by amplifying a detectable signal that is produced by the analyte. In some embodiments, the sensitizer may physically bind to the analyte, and may therefore act as a ligand.

In some embodiments, the sensitizer may be a ligand (sensitizing ligand) that aids in detection of a metal ion by producing a photosensitive metal-ligand compound. For example, the metal-ligand compound may be capable of emitting visible light upon exposure to UV light. The light may be emitted via phosphorescence or fluorescence. In some embodiments, the intensity of the emitted light may be measured in situ within the peelable sampling film (e.g., without requiring removal from the peelable sampling film), and may be used to estimate or calculate the concentration of the metal-ligand compound. In some embodiments, the spectrum and/or wavelengths of light emitted by the metal-ligand complex may be used as a "fingerprint" to identify the metal ion, including its oxidation state. For example, when the analyte is an actinide metal ion, lanthanide metal ion, or mixture of actinide and/or lanthanide ions, the additive may include a sensitizing ligand that binds to each ion to form a metal-ligand complex capable of emitting a characteristic fluorescence or phosphorescence spectrum that can be used to identify the type and/or concentration of the actinide ions in the analyte. Non-limiting examples of actinide metals that may form ions and metal-ligand complexes capable of emitting light may include actinium (Ac), thorium (Th), protactinium (Pa), uranium (U), neptunium (Np), plutonium (Pu), americium (Am), curium (Cm), berkelium (Bk), and californium (Cf). Non-limiting examples of lanthanide metals that may form ions and metal-ligand complexes capable of emitting light may include lanthanum (Ln), cerium (Ce), praseodymium (Pr), neodymium (Nd), promethium (Pm), samarium (Sa), europium (Eu), gadolinium (Gd), terbium (Tb), dysprosium (Dy), holmium (Ho), erbium (Er), thulium (Tm), ytterbium (Yb), and lutetium (Lu). Any suitable methods of selecting suitable sensitizers and producing and analyzing such spectra may be used.

In some embodiments, for example when the analyte is a biological sample (e.g., pathogens (including, e.g., bacteria), proteins, DNA, fingerprints), the additive may include a non-ionic detergent capable of solvating the biological sample in a form suitable for later biological amplification and/or analysis. For example, in some embodiments, the non-ionic detergent may be based on polyoxyethylene or glycoside. Non-limiting examples of the non-ionic detergent may include variants of Tween® (Croda International PLC, Snaith, United Kingdom), Triton® (Dow Chemical Co., Midland, MI), octyl thioglucoside, Brij® (Croda International PLC, Snaith, United Kingdom), etc., all available from Sigma-Aldrich (St. Louis, MO).

In some embodiments, when the additive is a non-ionic detergent, the non-ionic detergent may be included at an amount of about 1 wt % to about 50 wt % based on the total weight of the liquid gel, for example, about 10 wt % to about 40 wt % or about 20 to about 30 wt %. In some embodiments, when the non-ionic detergent includes polyethylene glycol (PEG), such as PEG-8000 (having an average molecular weight of 8,000 g/mol), the PEG may be included in an amount of about 1 wt % to about 20 wt %, for example, about 5 wt % to about 15 wt %, or about 8 wt % to about 12 wt % based on the total weight of the liquid gel. In some embodiments, when the non-ionic detergent includes a Triton-based detergent, such as Triton X-100 (Dow Chemical, Midland, MI) the Triton may be included in an amount of about 1 wt % to about 10 wt %, for example, about 3 wt % to about 8 wt %, or about 4 wt % to about 6 wt % based on the total weight of the liquid gel.

In some embodiments, when the biological sample includes a metal ion, such as $Na^+$, $Ca^+$, $Zn^{+2}$, $Mg^{+2}$, $Cu^{+2}$, etc., the additive may include a ligand or chelant to isolate that metal ion as an analyte, or in some embodiments, to suppress or reduce the action of enzymes that might degrade the biological sample (for example, the action of nuclease enzymes on samples including nucleic acids). Non-limiting examples of such ligands or chelants may include EDTA, tris-acetic acid-EDTA (TAE), and ethyleneglycol bis(2-aminoethyl ether)-N,N,N',N' tetraacetic acid (EGTA). The amount (concentration) of the ligand or chelant is not particularly limited, and may be substantially similar to that used in various biological sample preparation methods in the related art. In some embodiments, for example, the concentration of chelant in a rapidly curable liquid gel used to collect biological samples may be about 0.1 mM to about 5 mM, or about 1 mM to about 3 mM (e.g., about 0.3 mg/mL to about 1 mg/mL of EDTA). The chelant may be added as a solid salt or as a solution.

In some embodiments, the additive may be used to enable detection of the analyte within the peelable sampling film. For example, the additive may impart a physical or chemical structure to the peelable sampling film that enables the sampling film to serve as a suitable substrate for a particular detection method. In some embodiments, for example, the additive may include nanoparticles or nanoconfined structures that may enable the use of surface enhanced Raman spectroscopy (SERS) to detect and identify an analyte while the analyte is embedded in the peelable sampling film (e.g., SERS-enabling nanoconfined structures). In SERS, the presence of nanoconfined structures in the substrate enhances Raman scattering of molecules absorbed on the substrate by a factor of about $10^5$ to about $10^{14}$, for example about $10^5$ to about $10^7$, or about $10^{12}$ to about $10^{14}$. Without being bound by the correctness of any particular mechanism or theory, it is believed that the substrate may exhibit surface plasmon oscillations that can amplify Raman scattering waves under selected resonance conditions. The detected Raman scattering serves as a "fingerprint" that can be used to identify the absorbed analyte, even when present in trace amounts. The analyte may be any small molecule including one or more covalent bonds, and in some embodiments, may include organic molecules associated with illegal drugs, explosives, chemical reagents, and nucleic acid sequences.

Non-limiting examples of the nanoconfined structures may include two-dimensional structures such as nanorods and nanopillars, and three-dimensional structures such as nanoparticles, nanospheres, etc. In some embodiments, the nanoconfined structures may be formed of silver (Ag), gold (Au), copper (Cu), platinum (Pt), palladium (Pd), aluminum (Al), or mixtures thereof, but embodiments of the present disclosure are not limited thereto. The size, shape, and dimensions of the nanoconfined structures may be selected according to their effect on Raman scattering enhancement. For example, the size of the particle may be selected to maintain the electrical conductance of the substrate while minimizing the excitation of non-radiative vibrational or rotational transitions. Any suitable method in the art for preparing such nanoconfined structures may be used. Any suitable method or device may be used to detect the Raman scattering, and in some embodiments, may include handheld Raman spectrometer devices.

The nanoconfined structures are physically adjacent and form a continuous network in order to enhance the Raman scattering of the absorbed molecules. In some embodiments, the nanoconfined structures may be selected for their ability to self-aggregate, or their susceptibility to control via application of electromagnetic fields. For example, the nanoconfined structures may be exposed to a magnet before and/or during curing of the rapidly curable liquid gel in order to induce their aggregation and uniform orientation. The magnet may have any suitable strength capable of inducing aggregation in the nanoparticles. In some embodiments, the magnet may be a permanent magnet. In some embodiments, the magnet may be an electromagnet.

In some embodiments, the additive may produce light (e.g., luminescence) in response to radiation, and may enable the peelable sampling film to serve as a light-based detector of radioactive analytes. For example, the additive may enable the peelable sampling film to act as a flexible in situ scintillator to detect radioactive samples captured therein. The term "scintillator" is used herein in its art-recognized sense to refer to a material that is capable of absorbing energy in the form of ionizing radiation and re-emitting that energy in the form of light. The type of radiation emitted by the analyte is not particularly limited, and may include alpha, beta, or gamma radiation, or a combination thereof. In some embodiments, for example when the analyte is an alpha emitter, the additive may enable the peelable sampling film to act as a scintillator capable of detecting radiation from the analyte that cannot be detected by other means, for example due to a lack of radiation penetration outside of the peelable sampling film. The additive may be any suitable molecule or combination of molecules capable of converting ionizing radiation into visible light. The additive may include a fluorescent dye that converts the ionizing radiation into fluorescence, and in some embodiments, may also include a wavelength shifter that shifts the wavelength of light emitted by the fluorescent dye to a more convenient detection wavelength, such as a wavelength in the visible spectrum. Non-limiting examples of fluorescent dyes may include p-terphenyl, 2-phenyl-5-(4-phenylphenyl)-1,3,4-oxadiazole (PBD), 2-(4-tert-butylphenyl)-5-(4-phenylphenyl)-1,3,4-oxadiazole (butyl PBD), and 2,5-diphenyloxazole (PPO). A non-limiting example of a wavelength shifter may include 1,4-bis-(5-phenyl-2-oxazolyl)benzene (POPOP). In some embodiments, the additive may include a combination of PPO and POPOP. In some embodiments, the additive may include a combination of p-terphenyl and POPOP. In some embodiments, when the additive acts as a scintillator, the fluorescent dye may be included in an amount of about 0.1 wt % to about 5 wt % based on the total weight of the liquid gel, for example, about 1 wt % to about 3 wt %, and the wavelength shifter may be included in an amount of about 0.01 wt % to about 2 wt % based on the total weight of the liquid gel, for example about 0.02 wt % to about 1 wt %, or about 0.04 wt % to about 0.5 wt %.

In some embodiments, the additive may include a viscosity-modulating material. In some embodiments, the viscosity-modulating material may be used to decrease the viscosity of the rapidly curable liquid gel so that it is better able to penetrate porous surfaces. In some embodiments, the viscosity-modulating material may be used to decrease or increase the viscosity of the rapidly curable liquid gel so that it is easier to apply to a sampling surface. Non-limiting examples of the viscosity-modulating additive may include fumed silicas. In some embodiments, the solvent additive described above may also act as a viscosity-modulating additive.

In some embodiments, inclusion of the additive may prevent, reduce, or compromise the curing properties of the liquid gel. Without being bound by any particular theory, it is believed that certain additives may prevent or reduce the rate of cross-linking of the polymer precursor mixture components by lowering their effective concentrations and thereby their ability to find reaction partners, and/or may inadvertently terminate the polymerization reactions by reacting with the polymer chain in place of the polymer precursor components.

However, when the additive is not included, or is included below a threshold amount, the UV-curable liquid gel may have compromised ability to efficiently collect the target analyte from the sampling surface. Therefore, in some embodiments, the monomer(s), oligomer(s), photo-initiator(s), and additives are present in the UV-curable liquid gel in concentrations sufficient to allow the precursor gel to cure into a sampling film with appropriate material characteristics within an amount of time suitable for efficient and effective sample collection (e.g., a few seconds to a few minutes), while still having a sufficient concentration of additive to achieve the desired functional characteristics of the sampling film (such as the ability to collect analytes (e.g., contaminants) from the sampling surface).

In some embodiments, as discussed above, a combination of two or more additives (such as a solvent and a chelant) may be used in order to loosen and collect an analyte (e.g., crystals of analyte embedded in the pores and/or cracks of a surface, or on the surface of a substrate). For example, a rapidly curable liquid gel including a combination of a solvent and a chelant may have similar functional characteristics as a rapidly curable liquid gel including a larger volume of solvent by itself, but may have different curing times, removal rates or other relevant properties. Those having ordinary skill in the art are capable of selecting or choosing between suitable additive compositions according to the principles described herein.

In some embodiments, when the rapidly curable liquid gel includes a mixture of components, for example, a mixture of two commercially available UV-curable coating compositions, a mixture of a commercially available UV-curable coating composition and additional monomers, oligomers, and/or photoinitiators, and/or a mixture of a polymer precursor mixture with a solvent, non-ionic detergent, or other additive, the mixture may be substantially homogeneous (e.g., the concentration of each component may not substantially vary throughout the mixture). In other embodiments, at least a portion of one component may form a suspension, colloidal solution, or inclusion bodies in the other components of the rapidly curable liquid gel.

Inclusion of a highly UV absorptive component in the liquid gel composition may decrease the penetration of UV light through the full depth of the liquid gel, such that the rate of curing is undesirably reduced and/or the gel cannot be fully cured. Therefore, in some embodiments, the monomer, oligomer, and additive(s) may be screened and selected to have a UV absorption (absorbance) intensity A equal to or less than that of the photoinitiator at the wavelengths used for curing of the liquid gel composition.

According to one or more embodiments of the present invention, a kit for collecting an analyte from a sampling surface may include the rapidly curable liquid gel according to embodiments of the present invention, and a stencil. The kit may further include an applicator tool for applying the rapidly curable liquid gel to a sample collection surface and/or a bag or container for sample transport and/or storage. In some embodiments, the kit may further include a device to enable rapid curing. In some embodiments, when the rapidly curable liquid gel is polymerized by exposure to water and/or water vapor, the device may be a device capable of producing a water mist or spray, such as a spray bottle or other suitable atomizer or vaporizer. In some embodiments, when the rapidly curable liquid gel is polymerized using a cure activator component, the device may include a spatula or other article for mixing the cure activator component into the rapidly curable liquid gel. In some embodiments, when the rapidly curable liquid gel is UV-curable, the device may be a UV light source.

The stencil may be used to reproducibly control the sampling surface area and to aid in removal of the sampling film after curing of the liquid gel. For example, the stencil may be placed over the sample collection surface in the area intended for sample collection, and functions as a guide for the application of the liquid gel, as well as a structural support for removing the peelable sampling film after the curing process is complete.

In some embodiments, the stencil may be formed of a substrate that is flexible, tear-resistant, and transparent to UV radiation at the wavelengths necessary for initiation of photopolymerization reactions (e.g., the absorption wavelengths of the photoinitiators). For example, the substrate may be formed of a suitable polymer, polysiloxane, plastic, or the like.

In some embodiments, a portion of the stencil surface on the side adjacent to the sampling surface may be coated with an adhesive. The adhesive may be sufficiently strong to overcome gravity and enable temporary attachment to the surface, regardless of sampling surface orientation, yet have appropriate release characteristics to allow for removal of the stencil and any adjacent cured sampling film without tearing or damaging either the plastic substrate, the sampling film, or the sampling surface. A second portion of the stencil surface on the side adjacent to the sampling surface and contiguous with at least one edge of the stencil may not be coated with an adhesive. This second portion of the stencil surface can therefore act as a tab that can be easily grasped and pulled by a user, such that the stencil may be separated from (e.g., peeled off) the sampling surface after the gel has cured into a sampling film. In some embodiments, the stencil may be formed of substantially the same material as Redi-Tag® Write-On Self-Stick Index Tabs (available from Redi-Tag Corp., Nashville, TN).

The plastic substrate and adhesive should not contain contaminants (e.g., heavy metals) that might interfere with subsequent analysis of the sample. Accordingly, different stencil materials may be selected for different applications or for use with different analytical methods.

The thickness of the stencil is not particularly limited, and can be any thickness suitable for controlling and containing dispersion of the liquid gel prior to curing, while remaining sufficiently transparent to UV radiation to allow passage of any UV light needed to effect curing of the gel. In other words, the stencil may be any thickness as long as it does not interfere with curing, and enables subsequent peeling and pick up of the cured sampling film. In some embodiments, for example, the thickness of the stencil may be from 0.01 mm to 1 mm, and in some embodiments, 0.1 mm to 0.2 mm.

In some embodiments, the stencil may be perforated or may contain holes, grids, openings, etc. through which portions of the curable liquid gel can pass to make direct contact with the sampling surface. The size, shape, and density of the perforations, holes, etc. are not particularly limited, and can be adjusted or selected (e.g., depending on the viscosity of the gel) to allow the gel to seep through the holes and underneath the stencil. As described above, the stencil may be made of a UV-transparent substrate, such that UV-curable liquid gel located both above and underneath the stencil may be cured upon exposure to UV light. When the liquid gel is cured, the stencil is thereby embedded within the cured sampling film. Accordingly, when a user peels the stencil off the sampling surface, the attached sampling film and embedded analyte are both cleanly and efficiently removed from the sampling surface (e.g., without tearing or leaving too much residue).

When the stencil is perforated or otherwise contains holes or openings, the holes may have any suitable size and shape, without limitation. For example, the holes may be round, rectangular, ovular, or any other shape, and may have any suitable dimensions. For example, in some embodiments, the holes or openings may be generally round and be about 0.1 mm to about 10 mm in diameter; for example, about 0.5 mm to about 6 mm in diameter. In some embodiments, the holes may be generally round and about 1 mm to about 2.5 mm in diameter. The holes or openings may also be arranged in the stencil in any suitable manner, without limitation. For example, the holes may be packed in a rectangular grid (square packed), a hexagonal close-packed grid (hexagonally packed), a series of lines, a checkerboard-like grid, etc. In some embodiments, when the holes are periodically arranged, the holes may be spaced (e.g., may be created as a raster) about 0.5 mm to about 1.5 mm apart (edge to edge); for example, about 1 mm apart.

In some embodiments, the curable liquid gel and the stencil may be pre-supplied as a partially cured layer of the curable liquid gel on one side of the stencil substrate, such that the layer adheres to the stencil. In this case, the stencil may be applied to the sampling surface as usual, and the partially cured layer may be cured to a solid sampling film, for example, by exposure to additional UV light. However, embodiments of the present disclosure are not limited thereto, and the stencil may be applied to the sampling surface followed by application of the liquid gel to the stencil, curing of the gel, and removal of the stencil/sampling film.

The applicator tool is not particularly limited as long as it can suitably apply the rapidly curable liquid gel to the sampling surface, for example, as a uniform thin film. In some embodiments, the rapidly curable liquid gel may be applied with a syringe, spray bottle, brush, etc., depending on the material characteristics (e.g., viscosity) of the rapidly curable liquid gel. In some embodiments, for example, the liquid gel may simply be poured onto the stencil. This application technique may be particularly suitable when the gel has a viscosity sufficient to allow the liquid gel to wick or spread across the stencil to cover the desired area.

The UV light source may be any suitable light source such as a lamp, light bulb, LED, laser, and the like. In some embodiments, the UV light source may include a portable light source, such as a pocket UV lamp. The irradiation wavelengths emitted by the light source (e.g., the pocket UV lamp) may be any suitable wavelengths capable of initiating curing of the liquid gel. For example, in some embodiments, the irradiation wavelengths emitted by the UV light source may be about 365 nm and about 395 nm, however, embodiments of the present disclosure are not limited thereto. In some embodiments, the UV light source may include or be mounted in, for example, a portable stand or other structure capable of standardizing the distance at which the UV light source is held from the rapidly curable liquid gel.

The bag or container for sample storage is also not particularly limited, and may be any such bag or container capable of protecting the sampling films with embedded analyte from contamination and/or mechanical stress.

In some embodiments, the kit for collecting an analyte from a sampling surface may further include a device for analyzing the analyte. The device may be handheld or portable. In some embodiments, for example, the kit may further include an XRF spectrometer. In some embodiments, for example, when the rapidly curable liquid gel composition and/or cured gel includes an additive including nanoparticles or nanoconfined structures, the kit may further include a Raman spectrometer. In some embodiments, for example, when the rapidly curable liquid gel composition and/or cured gel includes an additive that produces light (e.g., luminescence) in response to radiation, such as a luminescent metal-ligand compound, a fluorescent dye, and/or wavelength shifter, the kit may further include a device for measuring photoluminescence, such as a photomultiplier tube in a dark, enclosed sample chamber.

According to one or more embodiments of the present invention, a method of using the kit (e.g., a method of collecting an analyte from a sampling surface using the kit) includes: applying the stencil to a sampling surface; applying the rapidly curable liquid gel to the stencil; and curing the rapidly curable liquid gel on the stencil to form a sampling film. The method may further include removing the stencil and sampling film from the sampling surface after cure; and storing the sampling film in a container for transport and/or storage.

Applying the stencil to the sampling surface and applying the rapidly curable liquid gel to the stencil may be accomplished as discussed above in connection with the description of the kit.

Curing the rapidly-curable liquid gel on the stencil to form a sampling film may include irradiating the UV-curable liquid gel with UV light until the liquid gel is sufficiently cured. As used herein, "sufficiently cured" refers to the formation of a cured sampling film that leaves behind minimal or substantially no residue from the liquid gel when the sampling film is removed from the sample collection surface. The time required for irradiation may be less than 45 seconds, and in some embodiments, about 3 seconds to about 30 seconds, and in some embodiments, 5 seconds to about 10 seconds, depending on the composition and properties of the UV-curable liquid gel. However, it is understood that different compositions of the liquid gel may require different irradiation times or curing methods, and that the present invention is not limited to a particular irradiation time or curing method. In some embodiments, the total time required for application and curing of the liquid gel may be less than about 10 minutes, or less than about 5 minutes, for example, about 30 seconds to about 3 minutes, or about 1 minute to about 2 minutes.

In some embodiments, the curing of the liquid gel may further involve additional processing during curing. In some embodiments, for example, when the liquid gel includes nanoconfined structures, as described herein, the liquid gel may be exposed to a magnetic or electric field prior to and/or during curing in order to induce aggregation and/or alignment of the nanoconfined structures. In some embodiments, the liquid gel may be exposed to a permanent magnet, and in some embodiments, the liquid gel may be exposed to an electromagnet. Any exposure duration and magnetic or electric field strength may be used as long as it induces a suitable degree of aggregation, and those of ordinary skill in the art are capable of determining such parameters according to the principles described herein.

Removing the stencil and sampling film from the sampling surface and storing the sampling film in a container may be accomplished as discussed above in connection with the description of the kit.

The analyte(s) embedded in the sampling film may be processed and identified using any suitable method available in the art. The method choice may depend on the size and physical form of the analyte, the type or kind of analyte, and the effect of the peelable sampling film on the detection technique (e.g., whether the peelable sampling film is integral to the detection technique, as described herein in connection with the SERS-enabling nanoconfined structures and the scintillation-enabling fluorescent dyes, or alternatively must be separated from the analyte to obtain sufficient detection signal). In some embodiments, the analyte may be detected and analyzed in situ, without removal from the peelable sampling film. In some embodiments, the analyte may be removed or extracted from the peelable sampling film for detection and analysis. Any suitable extraction method may be used. In some embodiments, for example, the peelable sampling film containing the analyte may be washed and/or suspended in a solvent to preferentially dissolve the analyte. In some embodiments, the peelable sampling film may be shredded, pulverized, or otherwise broken down into smaller pieces to thereby increase the surface area exposed to the solvent and improve the extraction efficiency. In some embodiments, the peelable sampling film containing the analyte may be fully dissolved, and the polymer components and analyte separately dissolved into immiscible solvents.

The following examples and experimental data are provided for illustrative purposes only, and do not limit the scope of the embodiments of the present invention.

Figure 1B:
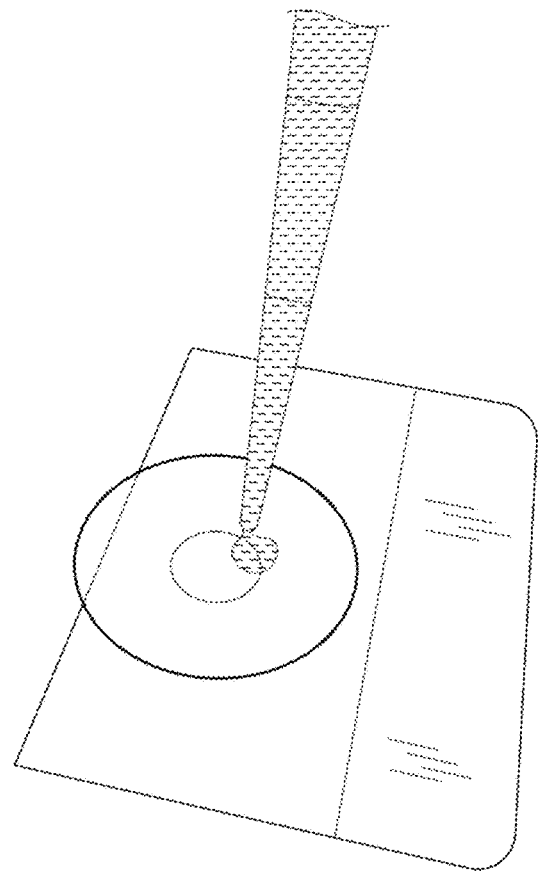
Figure 1C:
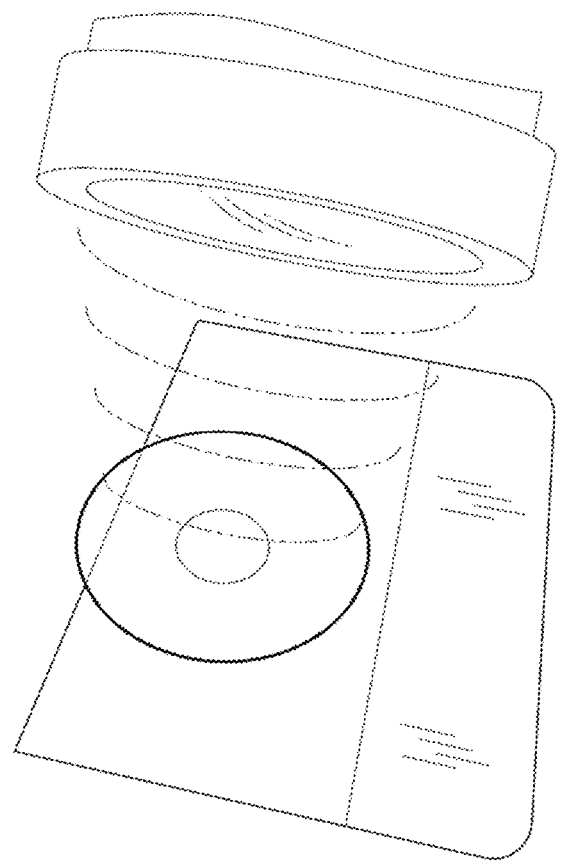
Figure 1D:
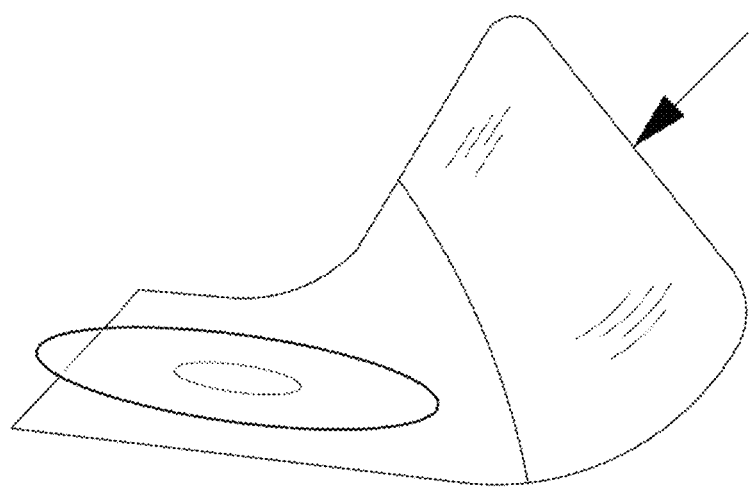

FIGS. 1A through 1D depict various steps in an example step-by-step method for collecting an environmental sample according to embodiments of the present disclosure. However, it will be understood that embodiments of the present disclosure are not limited to the example method shown in FIGS. 1A through 1D, and that those of ordinary skill in the art are capable of selecting appropriate stencils, curing gels, and curing methods as described herein, based on the specific application and the desired sampling film. FIG. 1A shows a sampling surface that is a round aluminum blank (1" diameter) containing a ring in the middle, which is the dried residue from a drop (approx. 50 µL) of aqueous solution containing 200 ppm uranyl, 400 ppm nitric acid, and blue organic food dye (added for ease of visualization). A stencil made from a Redi-Tag® Write-On Self-Stick Index Tab (obtained from Redi-Tag Corp., Nashville, TN) perforated by a pushpin over a 1 cm×1 cm area is applied to the sampling surface, such that the perforated area of the stencil is vertically adjacent to a portion of the residue (as made visible by the blue food dye). FIG. 1B shows the application of <1 mL of a UV-curable liquid gel (via pipette) onto the surface of the stencil over the pushpin-perforated area. FIG. 1C shows the curing of the UV-curable liquid gel on the stencil by applying a UV light for about 30 seconds. FIG. 1D shows removal of the stencil and sampling film from the sampling surface by grasping and pulling the portion of the stencil that does not include adhesive (opaque region, marked by arrow).

Figure 2:
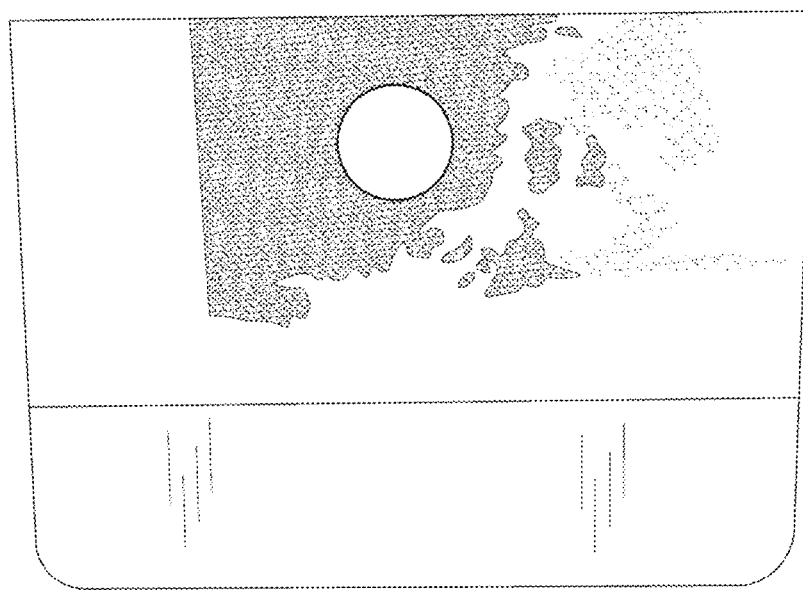
FIG. 2 is a photographic image showing an example sampling device used to collect explosive material residue from a blasting barrel, according to embodiments of the present disclosure.

FIG. 2 is a photographic image showing an example embodiment of a sampling film used to collect explosive material residue from a blasting barrel.

EXAMPLES

The following Examples and Comparative Examples are provided for illustrative purposes only, and are not to be construed as limiting the embodiments of the present disclosure.

Example 1-1 and Comparative Examples 1-1 and 1-2

Sampling surfaces were prepared by depositing and evaporating solutions of uranyl nitrate on brass sampling surfaces. The uranium content of each sampling surface was measured at 19 µg. The brass sampling surfaces were then sampled as follows.

Example 1-1

A UV-curable liquid gel was prepared by mixing UV733 (obtained from General Chemical Corp, Brighton, MI) and Tangent 20109 (obtained from Tangent Industries, Inc., Torrington, CT) in a 1:1 ratio and subsequently adding 25 vol % of ethanol. The UV-curable liquid gel was applied to a stencil on one of the brass sampling surfaces, and was irradiated with UV light for about 30 seconds. The UV curing was initiated within about 10 seconds after the initial application. The cured sampling film was then removed from the sampling surface.

Comparative Example 1-1

A cotton swipe was wiped over a second brass sampling surface.

Comparative Example 1-2

DeconGel (obtained from Metis Scientific, Honolulu, HI) was applied to a third brass sampling surface. DeconGel is not rapidly curable and therefore was allowed to dry in ambient air for about 6 hours before peeling. The cured sampling film was then removed from the sampling surface.

Figure 3:
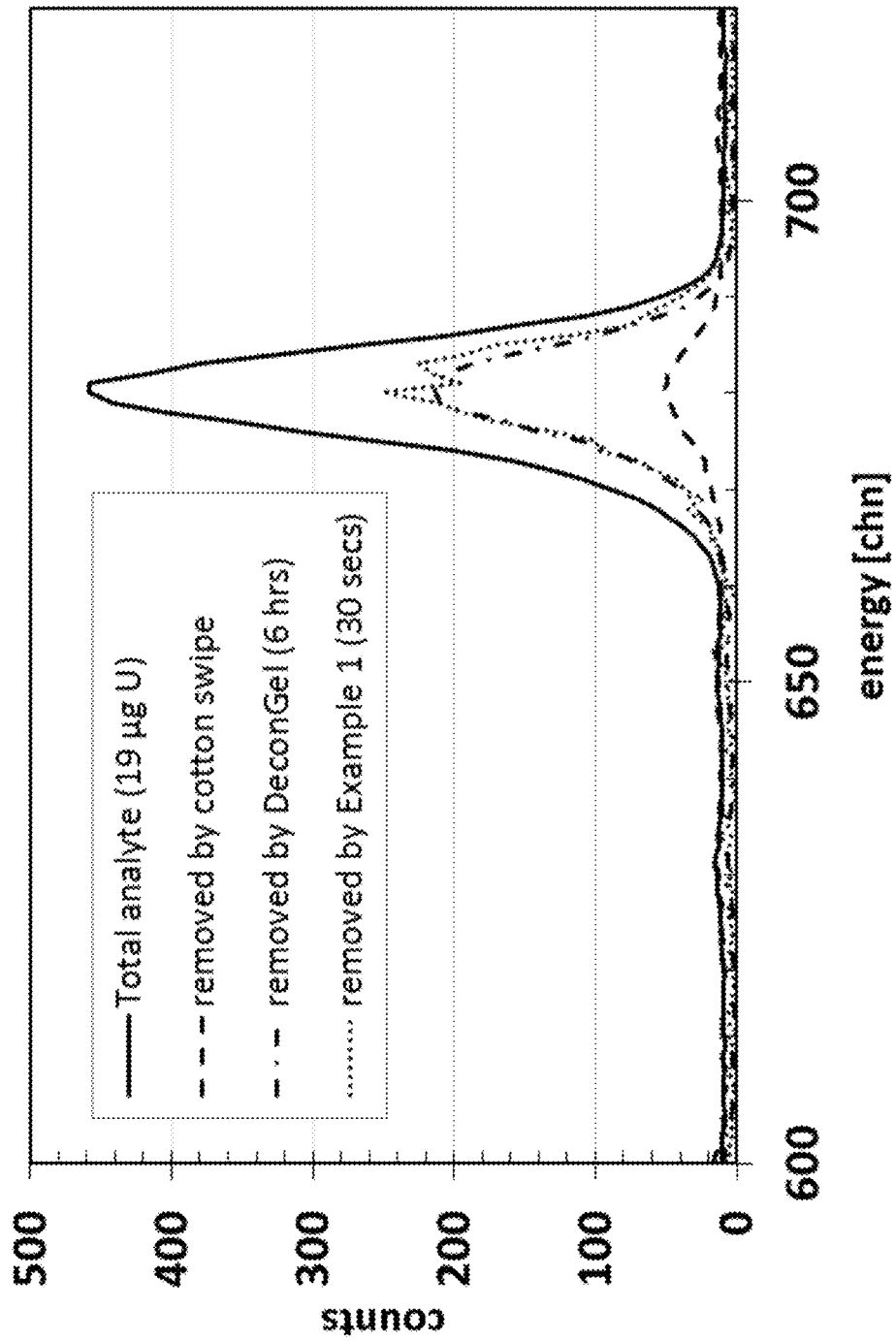
FIG. 3 is a graph comparing the x-ray fluorescence (XRF) spectra (specifically around the uranium Lα peak at 13.614 keV) of uranyl nitrate samples collected from a brass sampling surface via cotton swipe, DeconGel (Metis Scientific, Honolulu, HI), and the rapidly cured liquid gel composition according to Example 1-1, according to embodiments of the present disclosure.

XRF spectra were collected using a handheld pXRF spectrometer (Bruker AXS S1PXRF, Karlsruhe, Germany). FIG. 3 is a graph comparing the X-ray fluorescence (XRF) spectra (specifically around the uranium Lα peak at 13.614 keV) of the brass sampling surface before sampling ("total contamination") and of the samples obtained via cotton swipe (according to Comparative Example 1-1), DeconGel (according to Comparative Example 1-2), and the UV-curable gel (according to Example 1-1). The area of the peak is proportional to the amount of detected uranium. The UV-curable liquid gel of Example 1-1 and the DeconGel of Comparative Example 1-2 were each observed to have uranium amounts, and therefore sampling efficiencies of about 50% of the total uranium residue, while the cotton swipe of Comparative Example 1-1 was observed to have the lowest sampling efficiency (less than 10%). As such, the UV-curable liquid gel of Example 1-1 exhibited improved sampling efficiency compared to the cotton swipe of Comparative Example 1-1, and comparable sampling efficiency to the DeconGel of Comparative Example 1-2 in only a fraction of the curing time.

Examples 2-1 Through 2-29

Additional UV-curable liquid gels according to embodiments of the present disclosure were prepared according to the compositions described in Table 1.

TABLE 1

| Examples | Oligomers | Monomers | Photoinitiators | Additives |
|---|---|---|---|---|
| 2-1 to 2-3 | 2-carboxyethyl acrylate oligomers (5 mL) | Di(ethylene glycol) ethyl ether acrylate (5 mL), isobornyl acrylate (3 mL), tetrahydrofurfuryl acrylate (7 mL) | 4-(dimethylamino)benzophenone (0.3 g in Example 2-1; 0.4 g in Example 2-2; 0.5 g in Example 2-3) | |
| 2-4 to 2-6 | 2-carboxyethyl acrylate oligomers (5 mL) | Di(ethylene glycol) ethyl ether acrylate (5 mL), isobornyl acrylate (3 mL), tetrahydrofurfuryl acrylate (7 mL) | 4-(dimethylamino)benzophenone (0.3 in Example 2-4; 0.4 in Example 2-5; 0.5 g in Example 2-6) | Fumed Silica (0.5 g) |
| 2-7 to 2-10 | 2-carboxyethyl acrylate oligomers (9 mL) | Tetrahydrofurfuryl acrylate (1 mL) | Thioxanthen-9-one (0.01 in Example 2-7; 0.03 in Example 2-8; 0.1 in Example 2-9; 0.3 g in Example 2-10) | |
| 2-11 to 2-13 | 2-carboxyethyl acrylate oligomers (1 mL) | Tetrahydrofurfuryl acrylate (9 mL) | Thioxanthen-9-one (0.01 in Example 2-11; 0.03 in Example 2-12; 0.1 in Example 2-13; 0.3 g in Example 2-14) | |
| 2-15 to 2-17 | 2-carboxyethyl acrylate oligomers (5 mL) | Tetrahydrofurfuryl acrylate (5 mL) | Thioxanthen-9-one (0.3 in in Example 2-15; 0.5 in Example 2-16; 0.7 g in Example 2-17) | |
| 2-18 to 2-20 | 2-carboxyethyl acrylate oligomers (3 mL) | Tetrahydrofurfuryl acrylate (7 mL) | Thioxanthen-9-one (0.3 in Example 2-18; 0.5 in Example 2-19; 0.7 g in Example 2-20) | |
| 2-21 to 2-23 | 2-carboxyethyl acrylate oligomers (7 mL) | Tetrahydrofurfuryl acrylate (3 mL) | Thioxanthen-9-one (0.3 in Example 2-21; 0.5 in Example 2-22; 0.7 g in Example 2-23) | |
| 2-24 | 2-carboxyethyl acrylate oligomers (9 mL) | Tetrahydrofurfuryl acrylate (1 mL) | Thioxanthen-9-one (0.02 g) | |
| 2-25 | 2-carboxyethyl acrylate oligomers (9 mL) | Tetrahydrofurfuryl acrylate (1 mL) | Thioxanthen-9-one (0.02 g) | EDTA (1 g) |
| 2-26 | 2-carboxyethyl acrylate oligomers (9 mL) | Isobornyl acrylate (1 mL) | Thioxanthen-9-one (0.02 g) | |
| 2-27 | 2-carboxyethyl acrylate oligomers (9 mL) | Isobornyl acrylate (1 mL) | Thioxanthen-9-one (0.02 g) | EDTA (1 g) |
| 2-28 | 2-carboxyethyl acrylate oligomers (9 mL) | Di(ethylene glycol) ethyl ether acrylate (1 mL) | Thioxanthen-9-one (0.02 g) | |
| 2-29 | 2-carboxyethyl acrylate oligomers (9 mL) | Di(ethylene glycol) ethyl ether acrylate (1 mL) | Thioxanthen-9-one (0.02 g) | EDTA (1 g) |

Each of the compositions according to Examples 2-1 through 2-29 were mixed and cured to yield a peelable sampling film according to embodiments of the present disclosure.

Examples 3-1 Through 3-3

A series of rapidly curable liquid gel compositions (Examples 3-1 through 3-3) were made by mixing UV733 (General Chemical Corp, Brighton, MI) and Tangent 20109 (Tangent Industries, Inc., Torrington, CT) in ratios of 25:75 (Example 3-1), 50:50 (Example 3-2), and 75:25 (Example 3-3).

Example 3-4

A rapidly curable liquid gel composition was made by mixing UV733 with 30 wt % ethanol based on the total weight of the composition. The amount of ethanol in Example 3-4 was determined to be the maximum soluble amount.

Example 3-5

A rapidly curable liquid gel composition was made by mixing Tangent 20109 with 30 wt % ethanol based on the total weight of the composition. The amount of ethanol in Example 3-5 was determined to be the maximum soluble amount.

Example 3-6

A rapidly curable liquid gel composition was made by mixing 50 parts by weight of 2-carboxyethyl acrylate oligomer, 50 parts by weight of 2-[[(butylamino)carbonyl]oxy] ethyl acrylate, and 0.5 parts by weight of phenylbis(2,4,6-trimethylbenzoyl)-phosphine oxide (BAPO) as a photoinitiator.

Comparative Examples 3-1 Through 3-3

Commercially available DeconGel (Metis Scientific, Honolulu, HI) (Comparative Example 3-1), UV733 (Comparative Example 3-2), and Tangent 20109 (Comparative Example 3-3) were used without modification.

To analyze Examples 3-1 through 3-6 and Comparative Examples 3-1 through 3-3, uranyl nitrate samples were prepared by depositing 70 μL of 200 ppm uranyl nitrate solution on 1″-diameter circles made of steel or wood and allowing the solutions to dry on the steel or wood sampling surfaces overnight. An initial measurement of the uranium content of the sampling surface was taken by placing the sampling surface with the deposited uranyl nitrate solution directly on top of the XRF window, which is smaller than the area of the deposit. The measurement was repeated 3 times, rotating the sampling surface in the XRF window plane by 120 degree intervals, and the average of these three measurements was used as the effective concentration of deposited uranyl nitrate. The rapidly curable liquid gel compositions according to Examples 3-1 through 3-6 were then applied to respective sampling surfaces and cured using a method similar to that described herein in connection with FIGS. 1A through 1D and Example 1-1 (e.g., extraction of uranyl nitrate crystals). The cured sampling films were peeled away from the steel or wood sampling surface, and XRF measurements were taken of the sampling surface as well as the sampling films (after mounting on 5 μm Mylar foil). These measurements were also repeated three times with rotation of the sampling surface and reported as an average.

FIGS. 4A to 4C show representative XRF spectra corresponding to extraction of uranyl nitrate from a steel sampling surface using the rapidly curable liquid gel composition according to Example 3-6. FIG. 4A is a graph showing XRF spectra of the steel sampling surface prior to application of the liquid gel. The measurement was repeated three times as described above, and the average was taken as the amount of uranium deposited on the surface prior to extraction ("Pre-extraction"). FIG. 4B is a graph showing XRF spectra of the sampling surface after curing of the liquid gel and removal of the sampling film from the sampling surface. The measurement was repeated three times as described above, and the average was taken as a measurement of the remaining (e.g., un-extracted) uranium on the sampling surface. The uranium content of the steel sampling surface is noticeably decreased after sampling with the liquid gel of Example 3-6 ("Pre-extraction" vs. "Average"). FIG. 4C is a graph showing XRF spectra of the peeled sampling film mounted on Mylar foil. The measurement was repeated three times as described above, and the average was taken as a measurement of the uranyl content in the sampling film. In FIG. 4C, the baseline (background) of the "Steel, pre-extraction" spectrum is vertically shifted for ease of comparison to the measurement and average spectra.

The results (average of 10 replicates) are summarized in Table 2. Some measurement uncertainty can be caused by solvation and diffusion of the analyte in the liquid gel composition to occupy either a larger or smaller area, thus changing the apparent amount of uranium in the sampling film. Accordingly, to avoid this uncertainty, the reported extraction efficiencies in Table 2 are derived from the XRF measurements of the sampling surface before and after deposition of the rapidly curable liquid gel compositions. As the results shown in Table 2 are reported as average values for the 10 replicates, there is an amount of "relative error" in the reported single point values. That deviation (or "relative error") ranges between 5 and 10% such that the reported values should be read as the specific value±5 to 10%.

TABLE 2

| Liquid gel composition | Extraction efficiency from steel | Extraction efficiency from wood |
| --- | --- | --- |
| Example 3-1 (UV 733 + Tangent 20109, 25:75) | 70% | 20% |
| Example 3-2 (UV 733 + Tangent 20109, 50:50) | 61% | 7% |
| Example 3-3 (UV 733 + Tangent 20109, 75:25) | 67% | 12% |
| Example 3-4 UV733 + 30 wt % ethanol | 72% | n/a |
| Example 3-5 Tangent 20109 + 30 wt % ethanol | 44% | 13% |
| Example 3-6 (2-carboxyethyl acrylate oligomer + 2-[[(butylamino)carbonyl]oxy] ethyl acrylate + BAPO, 50:50:0.5) | 75% | 19% |
| Comparative Example 3-1 (DeconGel) | 92% | 58% |
| Comparative Example 3-2 (UV 733) | 51% | 8% |
| Comparative Example 3-3 (Tangent 20109) | 43% | 8% |

Table 2 shows that the liquid gel compositions according to Examples 3-1 through 3-6 showed extraction efficiencies ranging from about 75% to 44% for smooth steel surfaces, compared to less than 20% for porous wood surfaces. These extraction efficiencies were generally higher than those of Comparative Examples 3-2 and 3-3 for both surfaces. While the extraction efficiencies of these tested compositions did not match that of Comparative Example 3-1 (DeconGel), it must be noted that the curing times diverge by several orders of magnitude (e.g., 30 seconds for the Examples vs. 6 hours, or 21,600 seconds, for Comparative Example 3-1), and that the extended curing time for DeconGel is not compatible with the time constraints of active forensic sampling.

With respect to the liquid gel compositions according to Examples 3-1 to 3-3, which are mixtures of the liquid gel compositions according to Comparative Examples 3-2 and 3-3, it was found that the composition according to Example 3-1 had the highest extraction rates on both steel and wood. Without being bound by the correctness of any particular mechanism or theory, it is believed that a mixture of liquid gel compositions (e.g., UV733 and Tangent 20109) may form a network of regions (e.g., discrete regions), each of which regions includes one composition or another, such that the favorable characteristics of each composition are exhibited in different regions of the gel (e.g., different physical locations within the gel). For example, UV733 seeps into surfaces and cures within 10 seconds, while Tangent 20109 has a consistency more akin to gelatin and cures within 1 minute. The combination of the two may yield a liquid gel that is able to better penetrate surface pores and cracks and/or dissolve a higher concentration of the analyte than either in isolation, due to the solubility properties of the liquid gel and/or the semi-cured liquid gel.

With respect to the liquid gel compositions according to Example 3-4 and Comparative Example 3-2, the addition of 30 wt % ethanol to UV733 increased its extraction efficiency from steel from 51% to 72%. However, the liquid gel composition according to Example 3-4 soaked into the wood sampling surface and was unable to be cured and peeled. With respect to the liquid gel compositions according to Example 3-5 and Comparative Example 3-3, the addition of 30 wt % ethanol to Tangent 20109 left its extraction efficiency from steel only slightly higher (from 43% to 44%), and increased its extraction efficiency from wood from 8% to 13%. Without being bound by the correctness of any particular mechanism or theory, it is believed that Tangent 20109 has a higher viscosity than UV733, and as such, the composition according to Example 3-5 also had a higher viscosity than the composition according to Example 3-4, and was thus able to better enter the pores of the wood sampling surface without soaking through the wood. Accordingly, inclusion of a solvent additive (e.g., ethanol) in the rapidly curable liquid gel compositions was found to increase extraction efficiency in selected sampling applications.

The composition according to Example 3-6 showed the highest extraction efficiency from steel (75%) and an extraction efficiency from wood that was only slightly lower than the best performer in this category (19% vs 20%).

Examples 4-1 Through 4-4 and Comparative Example 4-1

A series of liquid gel compositions were tested for extraction of DNA (*E. Coli* genomic DNA) and bacteria (Arthobacteria) from a smooth, non-porous plastic laminate workbench surface. Sampling surfaces were prepared by pipetting stock solutions containing 100 ng of DNA in 10 µL of DNA elution buffer or $10^5$ Arthobacteria in 10 µL of LB medium (lysogeny broth, or Luria-Bertani medium) onto a clean and sterile workbench and allowing the solutions to dry for at least two hours.

Example 4-1

UV733 was used without modification as a rapidly curable liquid gel composition.

Example 4-2

A liquid gel composition was prepared by mixing UV733 with 0.1 mg/mL EDTA based on the total volume of the composition.

Example 4-3

A liquid gel composition was prepared by mixing UV733 with 10 wt % PEG8000 based on the total weight of the composition.

Example 4-4

A liquid gel composition was prepared by mixing UV733 with 5 wt % Triton X-100 based on the total weight of the composition.

In some experiments, the rapidly curable liquid gel compositions were cured over sampling surfaces prepared with DNA or bacteria as described above. In FIGS. 5-9, these samples are described as being "over DNA", or "over bacteria". In some experiments, the rapidly curable liquid gel compositions were cured over clean and sterile sampling surfaces containing substantially no DNA or bacteria to thereby provide positive controls. In FIGS. 5-9 and herein, these samples are described as "(blank)". In each experiment, 50 µL of the designated rapidly curable liquid gel composition was layered over a sampling surface, allowed to sit for no more than 10 seconds, cured under UV light for 15 seconds, and peeled from the workbench using tweezers.

The peeled sampling films were placed in a bead bashing (beating) tube (FastPrep-24 5G, MP Biomedicals, Santa Ana, CA) with 200 µL of Tris-HCl/EDTA (TLE) buffer and 750 µL of a suitable lysis buffer. Selected samples (as indicated below) were lysed at 6 m/s for 1.5 minutes (FastPrep-24 Classic, MP Biomedicals, Santa Ana, CA), and placed on ice for at least 1 minute. The sample tubes were then centrifuged at 10,000 G for 1 min, and the supernatant was subjected to DNA extraction and amplification using polymerase chain reaction (PCR).

A representative DNA extraction protocol is described as follows. 400 µL of the supernatant was transferred to a filter tube (Zymo-Spin IV Spin Filter, Irvine, CA) and centrifuged at 7,000×g for 1 minute to yield a filtrate. 1.2 mL of a fungal/bacterial DNA binding buffer was added to the filtrate, and 800 µL of the mixture was transferred to a second tube equipped with a filter column (Zymo-Spin II Spin Column, Irvine, CA) and centrifuged at 10,000×g for 1 minute. The filtrate from this second tube was discarded, and another 800 µL of the mixture was filtered using the same column in a second collection tube. 200 µL of a DNA pre-wash buffer was added to the column and centrifuged at 10,000×g for 1 minute. 500 µL of a fungal/bacterial DNA wash buffer was added to the column and centrifuged at 10,000×g for 1 minute. The column was transferred to a new collection tube and centrifuged at 10,000×g for 1 minute.

The column was transferred to a new 1.5 mL LoBind tube (Eppendorf, Hamburg, Germany) and allowed to sit uncapped for 1 minute. 35 µL of a DNA elution buffer was added to the column, allowed to sit for 1 minute, and then centrifuged at 10,000×g for 30 seconds to elute the column. The elutant was transferred via pipette to a new LoBind tube and stored at −20° C. for DNA amplification via quantitative polymerase chain reaction (qPCR).

qPCR was carried out using standard techniques using a TaqMan Gene Expression probe (Applied Biosystems, Foster City, CA), specifically, using a reaction volume of 25 µL held at an initial temperature of 95° C. for 10 minutes and then subjected to 40 cycles including a denaturing phase at 95° C. for 15 seconds and an annealing phase at 60° C. for 1 minute.

Comparative Example 4-1

Cotton swipes were used to provide a baseline comparison for the rapidly cured liquid gel compositions according to Examples 4-1 through 4-4. Cotton swipes according to this Comparative Example 4-1 were prepared by moistening a sterile wipe with a solution of 0.5 mL PBS with 0.05% Tween-20 (e.g., PBST) and storing in a 50 mL sample tube overnight.

Figure 5:
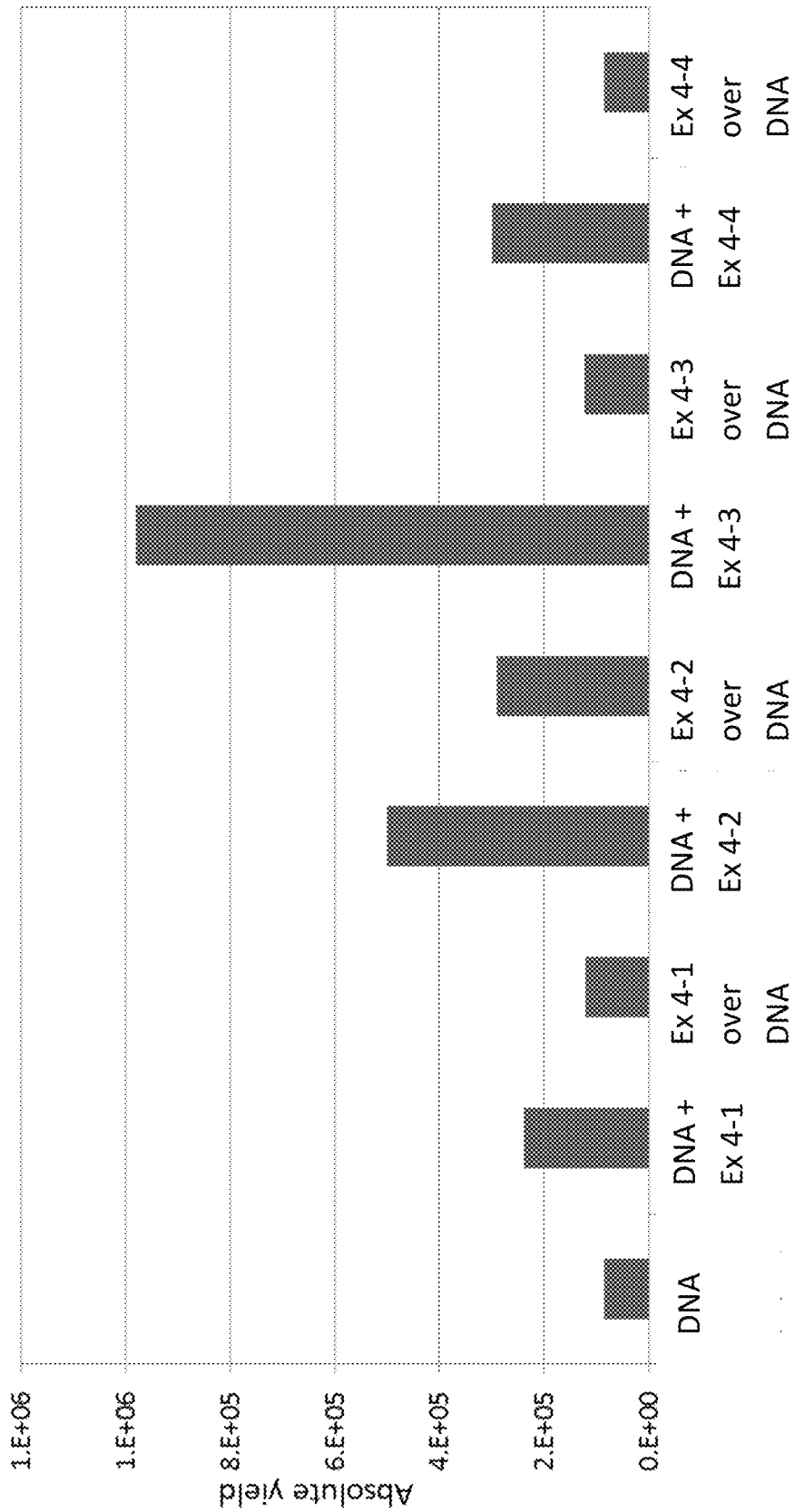
FIG. 5. is a chart comparing DNA extraction yields for the rapidly curable liquid gels according to Examples 4-1 through 4-4.
Figure 6:
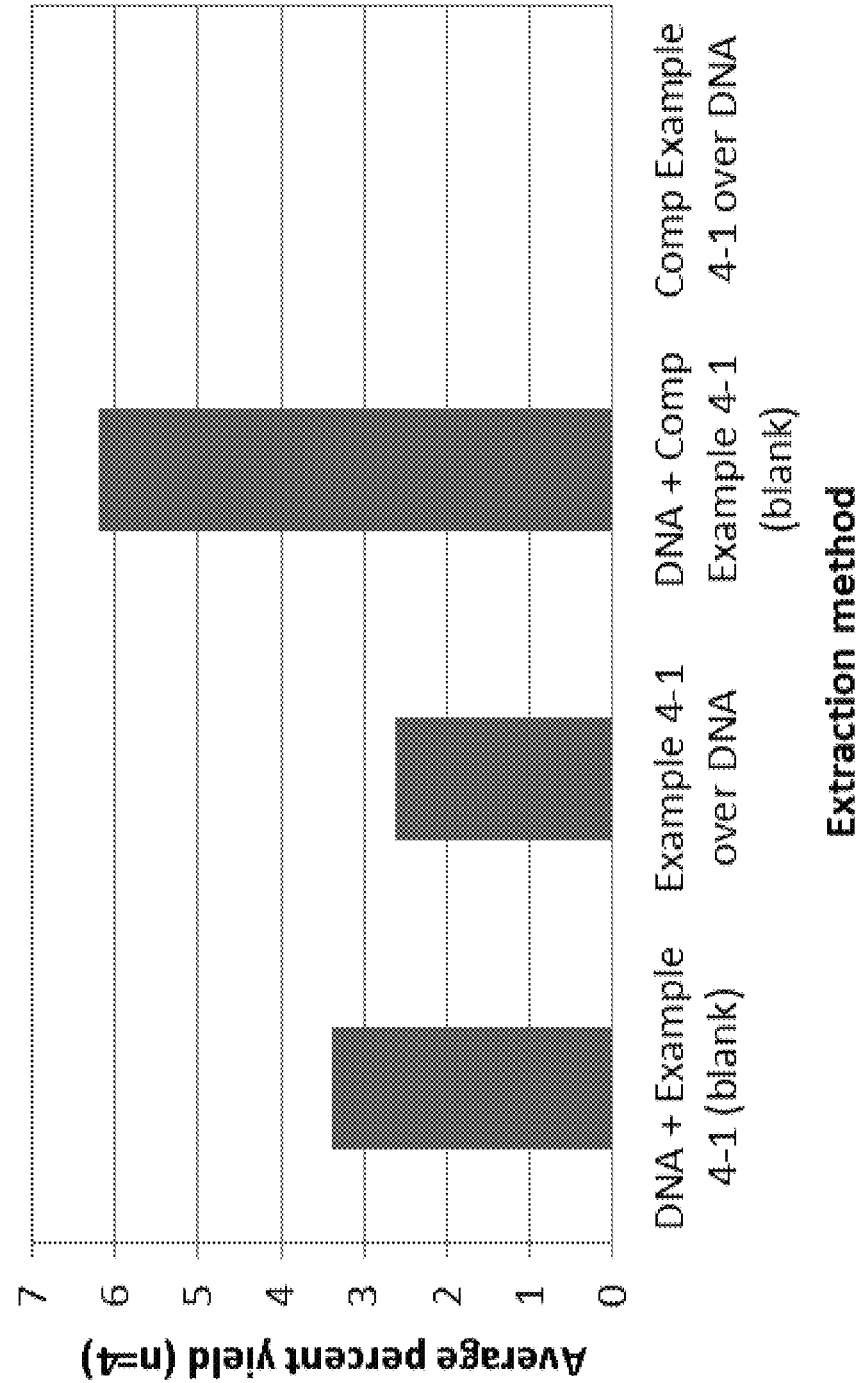
FIG. 6 is a chart comparing DNA extraction yields for the rapidly curable liquid gel according to Example 4-1 and the cotton swipe according to Comparative Example 4-1.
Figure 7:
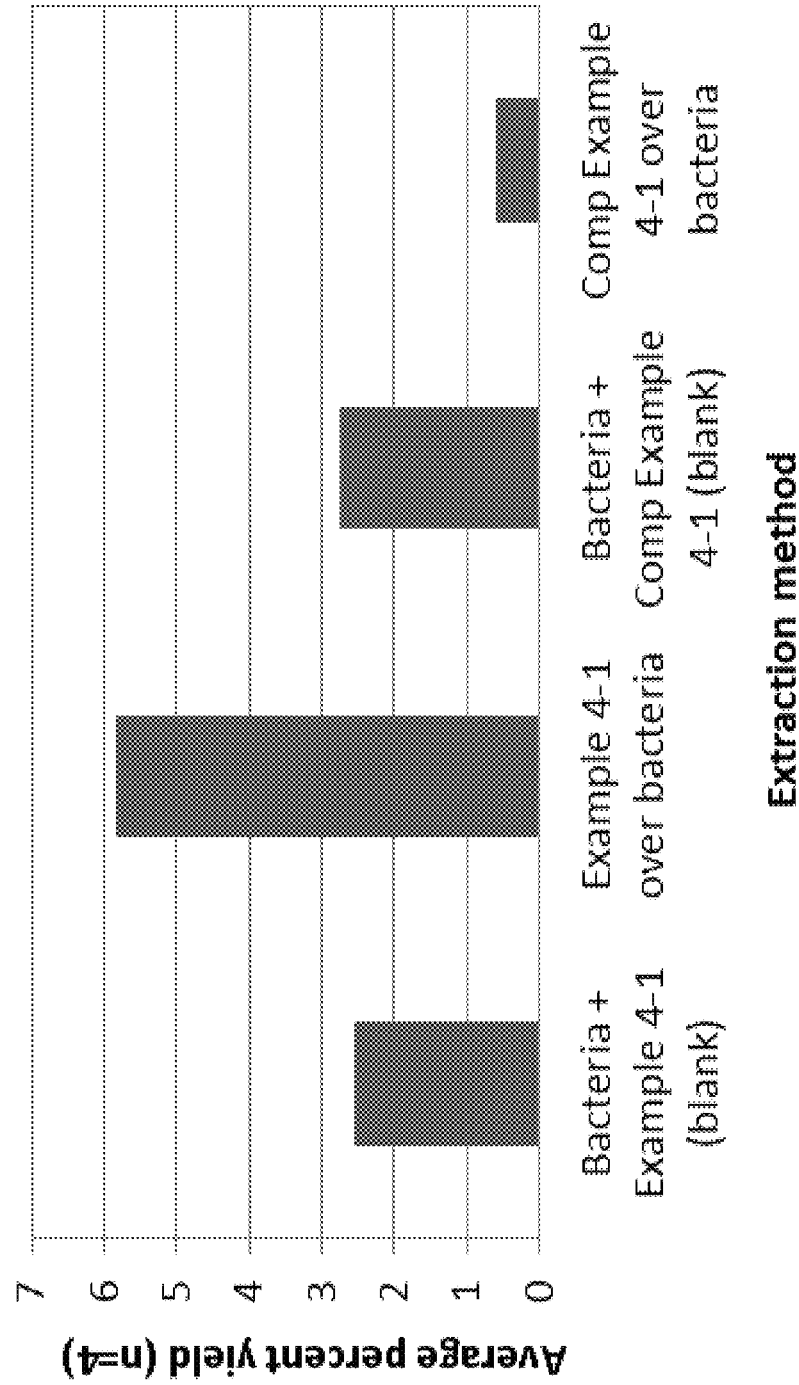
FIG. 7 is a chart comparing bacteria extraction yields for the rapidly curable liquid gel according to Example 4-1 and the cotton swipe according to Comparative Example 4-1.

In some experiments, the sterile wipe was wiped across sampling surfaces prepared with DNA or bacteria as described above. In FIGS. 5-7, these samples are described as being "over DNA", or "over bacteria". In some experiments, the sterile wipe was wiped across clean and sterile sampling surfaces containing substantially no DNA or bacteria to thereby provide positive controls. In FIGS. 5-7 and herein, these samples are described as "(blank)".

In each experiment, the sterile wipe was wiped across the sampling surface, replaced in the sample tube with 10 mL PBS, and vortexed at maximum speed for 20 minutes. The wipe was squeezed out and removed from the tube using forceps, and the remaining PBST was centrifuged at 4330×g at 4° C. for 10 minutes. The supernatant was decanted from the resulting pellet, and 200 µL of the pellet was placed in a bead bashing tube. 750 µL of lysis buffer was added to the tube, and the sample was lysed at 6 m/s for 90 seconds. The resultant was then subjected to DNA extraction and qPCR.

Positive control samples for DNA analysis were generally prepared by pipetting 100 ng DNA in 10 µL of DNA elution buffer directly into a bead bashing tube and subjecting that sample to the same lysis, extraction, and qPCR protocols described above. In FIGS. 5-7, these samples are indicated as "DNA". In some experiments, a 5 mm×5 mm piece of peeled sampling film (blank) or sterile wipe was added to the DNA prior to lysis and extraction.

Positive control samples for bacteria analysis was generally prepared by pipetting $10^5$ Arthobacteria in 10 µL of LB media directly into a bead bashing tube and subjecting that sample to the same lysis, extraction, and qPCR protocols described above. In FIGS. 6-7, these samples are indicated as "Bacteria". In some experiments, a 5 mm×5 mm piece of peeled sampling film (blank) or sterile wipe was added to the bacteria prior to lysis and extraction.

FIG. 5. is a chart comparing the DNA extraction yields for the rapidly cured liquid gels according to Examples 4-1 through 4-4. The positive control including only DNA was found to have a lower yield than the positive controls including DNA mixed with a cured sampling film (DNA+Ex 4-1, etc.), suggesting that the inclusion of a cured polymer in the sample may improve DNA extraction. The DNA extraction efficiencies of the polymers can be estimated by comparing the results of each "DNA+polymer" positive control with its corresponding "polymer over DNA" sample. The efficiency was calculated to be about 50% for the composition according to Example 4-1, 58% for the composition according to Example 4-2, 13% for the composition according to Example 4-3, and 30% for the composition according to Example 4-4. A comparison of the cured sampling film over DNA shows that the composition according to Example 4-2 (including 0.1 mg/mL EDTA) had improved extraction yields over the composition according to Example 4-1. The compositions according to Examples 4-3 and 4-4 did not appear to be substantially different from the composition according to Example 4-1. Without being bound by the correctness of any mechanism or theory, it is hypothesized that the detergent additives of Examples 4-3 and 4-4 were immiscible with UV733, and thus formed aqueous pockets that limited curing and pick up of DNA. As such, extraction yields may be improved by further modification of the rapidly curable liquid gel compositions, for example, by incorporating the detergent additives in solid form, reducing the amount of detergent additive to limit pocket formation, using a solvent to improve solvation of the detergent additive, etc.

FIG. 6 is a chart comparing the DNA extraction yields for the rapidly curable liquid gel composition according to Example 4-1 and the cotton swipe according to Comparative Example 4-1. Each reported percent yield is the calculated average of 4 replicates. The DNA extraction yield of the composition according to Example 4-1 is close to that of the positive control, in which the DNA is deposited directly in the tube, suggesting a high extraction efficiency. It should be noted that that experiment for DNA+Comp Example 4-1 shows an elevated amount of DNA due to the presence of natural DNA in the cotton swipe. However, the extraction efficiency of the cotton swipe was found to be near zero, demonstrating that rapidly curable liquid gel compositions according to embodiments of the present disclosure are capable of improved environmental sampling of DNA compared to conventional forensic methods.

FIG. 7 is a chart comparing the bacteria extraction yields for the rapidly curable liquid gel according to Example 4-1 and the cotton swipe according to Comparative Example 4-1. Each reported percent yield is the calculated average of 4 replicates. The bacteria extraction yield of the composition according to Example 4-1 is larger than that of the positive control, suggesting that more parts of the bacteria genome are being preserved and amplified in this case. Again, the extraction efficiency of the cotton swipe was found to be very low (e.g., less than ⅕ of the positive control), demonstrating that rapidly curable liquid gel compositions according to embodiments of the present disclosure are capable of improved environmental sampling of bacteria compared to conventional forensic methods.

Examples 5-1 and 5-2 and Comparative Example 5-1

Example 5-1

A rapidly curable liquid gel composition was made by mixing 50 parts by weight of EJ-309 (Eljen Technologies, Sweetwater, TX) as a liquid scintillator, 50 parts by weight of trimethylolpropane triacrylate, and 1 part by weight of phenylbis(2,4,6-trimethylbenzoyl)-phosphine oxide (BAPO).

Example 5-2

A rapidly curable liquid gel composition was made by mixing 100 parts by weight of EJ-309 (Eljen Technologies, Sweetwater, TX), 50 parts by weight of trimethylolpropane triacrylate, and 1 part by weight of BAPO.

Comparative Example 5-1

A rapidly curable liquid gel composition was made by mixing 50 parts by weight of 2-[[(butylamino)carbonyl]oxy] ethyl acrylate, 50 parts by weight of trimethylolpropane triacrylate, 20 parts by weight of EJ-309 (Eljen Technologies, Sweetwater, TX), and 1 part by weight of BAPO.

The rapidly curable liquid gel composition according to Examples 5-1 and 5-2 and Comparative Example 5-1 were applied to clean steel and wood sampling surfaces (containing no analyte deposits), cured, and peeled to confirm that all compositions were able to yield peelable sampling films from both kinds of surfaces.

The scintillation behavior of the cured and peeled sampling films were analyzed by placing each sampling film between a Americium-241 radiation source and a photomultiplier tube (PMT) in a dark box. A change in PMT count rate was taken to be indicative of luminescence produced by scintillation.

Figure 8:
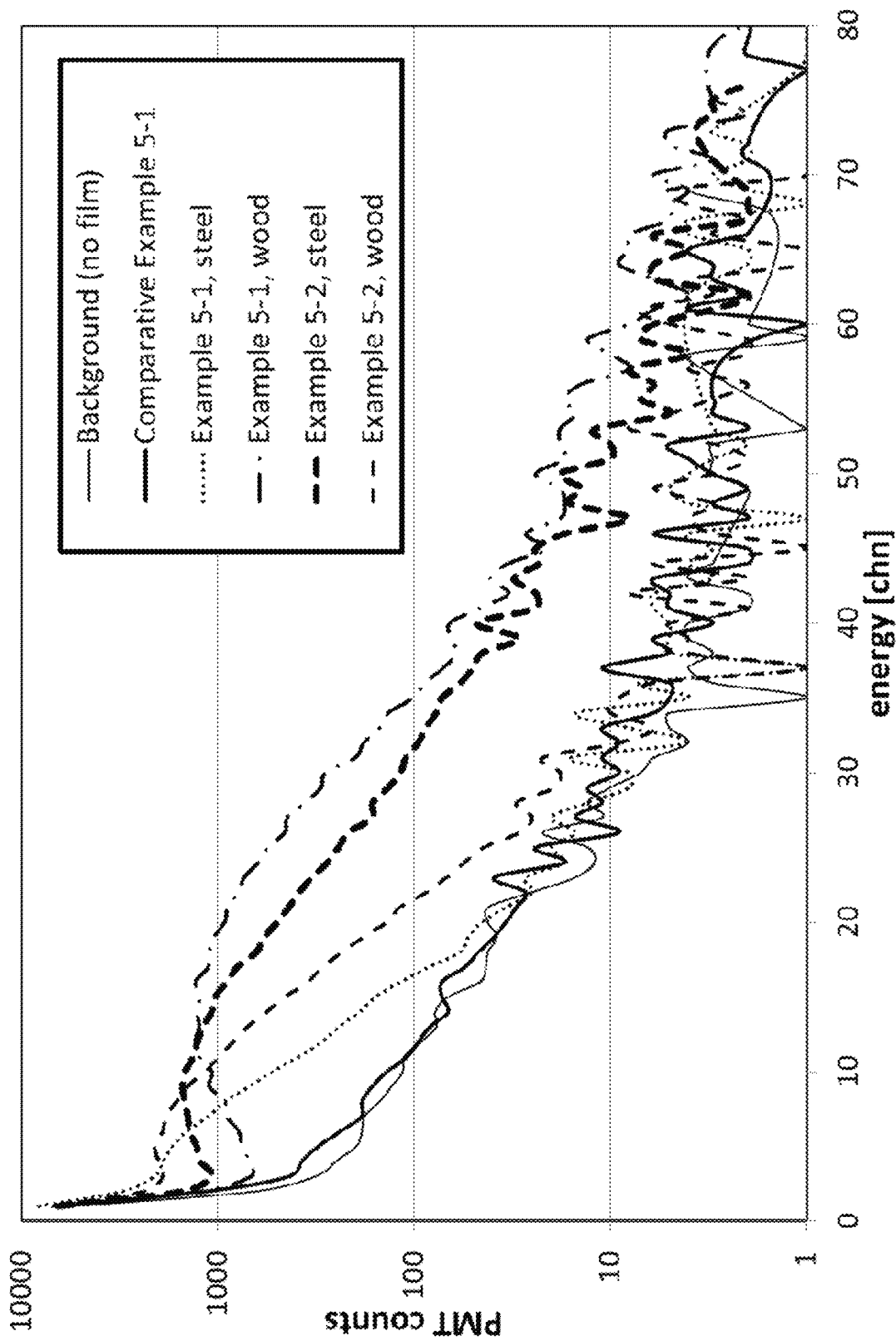
FIG. 8 is a log-linear graph of photomultiplier tube (PMT) counts with respect to photon energy (chn), as measured for peeled sampling films of rapidly cured liquid gel compositions including a liquid scintillator upon exposure to a radiation source, according to an embodiment of the present disclosure.

FIG. 8 is a log-linear graph of PMT counts with respect to photon energy (chn). The "Background" trace corresponds to the PMT response when no sampling film is placed between the radiation source and the PMT. The trace for the sampling film of Comparative Example 5-1 is similar to that of the Background trace, which suggests that Comparative Example 5-1 does not include a sufficient amount of a fluorescent dye to act as a scintillating material. All of the sampling films of Examples 5-1 and 5-2 showed a peak, or increase in PMT counts, between about 5 to about 60 chn, demonstrating that luminescence is generated by these sampling films in response to the radiation source, and that the peeled sampling films are able to act as scintillators.

As described herein, embodiments of the present disclosure provide various rapidly curable liquid gel compositions for collecting a wide range of analytes from a variety of sampling surfaces. Further, embodiments of the present disclosure provide an improved method of efficiently collecting such analytes or samples, even when present only in trace amounts (e.g., microsampling). The described compositions and methods of "active environmental sampling" enable improved sensitivity and reproducibility in the extraction, detection, and analysis of forensic evidence.

While certain exemplary embodiments of the present disclosure have been illustrated and described, those of ordinary skill in the art will recognize that various changes and modifications can be made to the described embodiments without departing from the spirit and scope of the present invention, and equivalents thereof, as defined in the claims that follow this description. For example, although certain components may have been described in the singular, i.e., "an" oligomer, "a" photoinitiator, and the like, one or more of these components in any combination can be used according to the present disclosure. Additionally, although some embodiments are described as including a UV-curable polymer precursor mixture or UV-curable gel or liquid, it is understood that any rapidly curable polymer precursor mixture, gel or liquid may be used in place of the UV-curable counterparts.

Also, although certain embodiments have been described as "comprising" or "including" the specified components, embodiments "consisting essentially of" or "consisting of" the listed components are also within the scope of this disclosure. For example, while embodiments of the present invention are described as comprising applying the stencil to the sampling surface; applying the UV-curable liquid gel to the stencil; and curing the UV-curable liquid gel on the stencil by irradiating the UV-curable liquid gel with UV light emitted by the UV lamp to form a sampling film, embodiments consisting essentially of or consisting of these actions are also within the scope of this disclosure. Accordingly, a method of using a kit for collecting an analyte from a sampling surface may consist essentially of applying the stencil to the sampling surface; applying the UV-curable liquid gel to the stencil; and curing the UV-curable liquid gel on the stencil by irradiating the UV-curable liquid gel with UV light emitted by the UV lamp to form a sampling film. In this context, "consisting essentially of" means that any additional components or process actions will not materially affect the product produced by the reaction.

As used herein, unless otherwise expressly specified, all numbers such as those expressing values, ranges, amounts or percentages may be read as if prefaced by the word "about," even if the term does not expressly appear. Further, the word "about" is used as a term of approximation, and not as a term of degree, and reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. For example, while the present disclosure may describe "an" oligomer or "a" photoinitiator, a mixture of such oligomers or photoinitiators can be used. When ranges are given, any endpoints of those ranges and/or numbers within those ranges can be combined within the scope of the present disclosure. The terms "including" and like terms mean "including but not limited to," unless specified to the contrary.

Notwithstanding that the numerical ranges and parameters set forth herein may be approximations, numerical values set forth in the Examples are reported as precisely as is practical. Any numerical value, however, inherently contains certain errors necessarily resulting from the standard variation found in their respective testing measurements. The word "comprising" and variations thereof as used in this description and in the claims do not limit the disclosure to exclude any variants or additions.

What is claimed is:

1. A composition for a rapidly curable liquid gel, the composition being configured to collect and preserve a sample that includes DNA from a sampling surface, and form a peelable coating to be removed from the sampling surface, the composition comprising:

a polymer precursor mixture comprising at least one of a monomer or an oligomer selected to polymerize upon application of energy from light and configured to form the peelable coating comprising the sample that includes DNA; and one or more additives selected to enhance extraction of the sample that includes DNA from the sampling surface in a form suitable for analysis of the sample that includes DNA after extraction.

2. The composition of claim 1, the composition further comprising a photoinitiator compound.

3. The composition of claim 1, wherein the one more additives comprise a non-ionic detergent based on polyethylene glycol (PEG) present in an amount from about 5 wt % to about 15 wt %.

4. The composition of claim 1, wherein the one or more additives comprise a non-ionic detergent.

5. The composition of claim 4, wherein the non-ionic detergent is selected to solvate the sample that includes DNA in a form suitable for amplification and the analysis of the sample that includes DNA after extraction.

6. The composition of claim 1, wherein the one or more additives comprise a non-ionic detergent based on polyoxyethylene or glycoside.

7. The composition of claim 1, wherein the one or more additives comprise a non-ionic detergent based on polyoxyethylene, polyoxyethylene ethers, polysorbates, polyethylene glycols, or octyl thioglucoside.

8. The composition of claim 1, wherein the at least one of the monomer or the oligomer is selected to provide a cure rate such that the composition will cure in about 10 minutes or less upon application of the energy from light.

9. The composition of claim 1, wherein the at least one of the monomer or the oligomer is selected to provide a cure rate such that the composition will cure in about 5 minutes or less upon application of the energy from light.

10. The composition of claim 1, wherein the at least one of the monomer or the oligomer is selected to provide a cure rate such that the composition will cure in about 3 minutes or less upon application of the energy from light.

11. The composition of claim 1, wherein the at least one of the monomer or the oligomer is selected to provide a cure rate such that the composition will cure in about 30 seconds or less upon application of the energy from light.

12. A composition for a rapidly curable liquid gel, the composition being configured to collect and preserve a sample that includes DNA from a sampling surface, the composition comprising:
   a polymer precursor mixture comprising at least one of a monomer or an oligomer selected to polymerize upon application of energy from light and configured to form a peelable coating comprising the sample that includes DNA; and
   one or more additives selected to enhance extraction of the sample that includes DNA from the sampling surface in a form suitable for analysis of the sample that includes DNA after extraction,
   the one more additives comprising a non-ionic detergent based on polyoxyethylene in an amount from about 5 wt % to about 15 wt %.

13. A composition for a rapidly curable liquid gel, the composition being configured to collect and preserve a sample that includes DNA from a sampling surface, the composition comprising:
   a polymer precursor mixture comprising at least one of a monomer or an oligomer selected to polymerize upon application of energy from light and configured to form a peelable coating comprising the sample that includes DNA; and
   one or more additives selected to enhance extraction of the sample that includes DNA from the sampling surface in a form suitable for analysis of the sample that includes DNA after extraction,
   the one or more additives comprising a non-ionic detergent based on glycoside, a chelant selected from among ethylene diamine, ethylene diamine tetraacetic acid, 4,5-dihydroxy-1,3-benzenedisulfonic acid, sodium citrate dehydrate, L-cysteine, diethylenetriaminepentaacetic acid (DTPA), acetoacetonate, oxalate and a combination thereof, nanoparticle structures, nanoconfined structures, a fluorescent dye, fumed silica, or a combination thereof.

14. The composition of claim 13, wherein the one or more additives comprise the non-ionic detergent based on glycoside.

15. The composition of claim 13, wherein the one or more additives comprise octyl thioglucoside.

16. The composition of claim 13, wherein the one or more additives comprise a chelant selected from among ethylene diamine, ethylene diamine tetraacetic acid (EDTA), 4,5-dihydroxy-1,3-benzenedisulfonic acid, sodium citrate dehydrate, L-cysteine, diethylenetriamine pentaacetic acid (DTPA), acetoacetonate, oxalate and a combination thereof.

17. The composition of claim 13, wherein the one or more additives comprise EDTA in an amount of about 0.1 g to about 2 g per 10 mL of the rapidly curable liquid gel.

18. The composition of claim 13, wherein the one or more additives comprise the fluorescent dye in an amount of 0.1 wt % to about 5 wt % based on the total weight of the liquid gel.

19. The composition of claim 13, wherein the one or more additives comprise fumed silica.

* * * * *